(12) United States Patent
Matthews

(10) Patent No.: US 8,309,552 B2
(45) Date of Patent: *Nov. 13, 2012

(54) IMMUNOMODULATING HETEROCYCLIC COMPOUNDS

(75) Inventor: Ian Richard Matthews, Abingdon (GB)

(73) Assignee: Medigene AG, Martinsried (DE)

( * ) Notice: Subject to any disclaimer, the term of this patent is extended or adjusted under 35 U.S.C. 154(b) by 206 days.

This patent is subject to a terminal disclaimer.

(21) Appl. No.: 12/545,902

(22) Filed: Aug. 24, 2009

(65) Prior Publication Data

US 2009/0312334 A1 Dec. 17, 2009

Related U.S. Application Data

(62) Division of application No. 11/845,837, filed on Aug. 28, 2007, now Pat. No. 7,598,247, which is a division of application No. 10/547,448, filed as application No. PCT/GB2004/001008 on Mar. 10, 2004, now Pat. No. 7,267,505.

(30) Foreign Application Priority Data

| Mar. 14, 2003 | (GB) | 0305876.5 |
| Aug. 19, 2003 | (GB) | 0319429.7 |

(51) Int. Cl.
| A01N 43/58 | (2006.01) |
| A61K 31/50 | (2006.01) |
| C07D 237/26 | (2006.01) |
| C07D 487/00 | (2006.01) |

(52) U.S. Cl. .................................... 514/248
(58) Field of Classification Search .............. 514/248; 544/234

See application file for complete search history.

(56) References Cited

U.S. PATENT DOCUMENTS

| 3,576,637 | A | 4/1971 | Suga et al. |
| 4,591,589 | A | 5/1986 | Gasc et al. |
| 5,061,705 | A | 10/1991 | Wuest et al. |
| 7,276,505 | B2 * | 10/2007 | Matthews ............. 514/248 |
| 7,566,713 | B2 | 7/2009 | Mathews |
| 7,598,247 | B2 | 10/2009 | Matthews |
| 2007/0213345 | A1 | 9/2007 | Matthews |
| 2009/0062289 | A1 | 3/2009 | Matthews |
| 2009/0221590 | A1 | 9/2009 | Matthews |
| 2009/0312334 | A1 | 12/2009 | Matthews |

FOREIGN PATENT DOCUMENTS

| EP | 0255892 | 2/1988 |
| EP | 0269030 | 6/1988 |
| GB | 629412 | 9/1949 |
| WO | 97/34893 | 9/1997 |
| WO | 99/00391 | 1/1999 |
| WO | 03/004485 | 1/2003 |
| WO | 03/004495 | 1/2003 |
| WO | WO 03/004495 | * | 1/2003 |
| WO | 2004/048378 | 6/2004 |
| WO | 2004/055014 | 7/2004 |
| WO | WO 2004/081011 | 9/2004 |
| WO | WO 2005/116033 | 12/2005 |

(Continued)

OTHER PUBLICATIONS

Huxley, et al., High-Affinity Small Molecule Inhibitors of T Cell Costimulation: Compounds for Immunotherapy, Chemistry & Biology, vol. 11, 1851-1858 (2004).*

(Continued)

Primary Examiner — Erich A Leeser
(74) Attorney, Agent, or Firm — Banner & Witcoff, Ltd.

(57) ABSTRACT

Compounds of formula (I) are inhibitors of CD80 and useful in immunomodulation therapy:

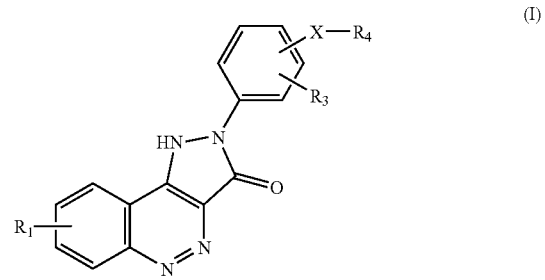

(I)

wherein $R_1$ and $R_3$ independently represent H; F; Cl; Br; $-NO_2$; $-CN$; $C_1$-$C_6$ alkyl optionally substituted by F or Cl; or $C_1$-$C_6$ alkoxy optionally substituted by F; $R_4$ represents a carboxylic acid group (—COOH) or an ester thereof, or $-C(=O)NR_6R_7$, $-NR_7C(=O)R_6$, $-NR_7C(=O)OR_6$, $-NHC(=O)NR_7R_6$ or $-NHC(=S)NR_7R_6$ wherein $R_6$ represents H, or a radical of formula -(Alk)$_m$-Q wherein m is 0 or 1, Alk is an optionally substituted divalent straight or branched $C_1$-$C_{12}$ alkylene, or $C_2$-$C_{12}$ alkenylene, or $C_2$-$C_{12}$ alkynylene radical or a divalent $C_3$-$C_{12}$ carbocyclic radical, any of which radicals may contain one or more —O—, —S— or —N($R_8$)— links wherein $R_8$ represents H or $C_1$-$C_4$ alkyl, $C_3$-$C_4$ alkenyl, $C_3$-$C_4$ alkynyl, or $C_3$-$C_6$ cycloalkyl, and Q represents H; $-NR_9R_{10}$ wherein $R_9$ and $R_{10}$ independently represents H; $C_1$-$C_4$ alkyl; $C_3$-$C_4$ alkenyl; $C_3$-$C_4$ alkynyl; $C_3$-$C_6$ cycloalkyl; an ester group; an optionally substituted carbocyclic or heterocyclic group; or $R_9$ and $R_{10}$ form a ring when taken together with the nitrogen to which they are attached, which ring is optionally substituted; and $R_7$ represents H or $C_1$-$C_6$ alkyl; or when taken together with the atom or atoms to which they are attached $R_6$ and $R_7$ form an optionally substituted monocyclic heterocyclic ring having 5, 6 or 7 ring atoms; and X represents a bond or a divalent radical of formula $-(Z)_n$-(Alk)- or -(Alk)-$(Z)_n$— wherein Z represents —O—, —S— or —NH—, Alk is as defined in relation to $R_6$ and n is 0 or 1.

48 Claims, No Drawings

FOREIGN PATENT DOCUMENTS

WO     WO 2007/096588     8/2007

OTHER PUBLICATIONS

West, Anthony R., Solid State Chemistry and Its Applications, Wiley, New York, 1988, 358.*

Ames & Bull, "Preparation of cinnoline-3, 4-dicarbonitrile and -dicarboxylic acid," Tetrahedron, vol. 37, No. 14, pp. 2489-2491, 1981.

Byun et al., "Preparation of polymer-bound pyrazoloneactive esters for combinatorial chemistry," Tetrahedron Letters, vol. 44, pp. 8063-8067, Oct. 2003.

ClinicalTrials.gov., http://clinicaltrials.gov/ct2/show/NCT00704119, last updated Nov. 4, 2008; downloaded Mar. 10, 2010.

Collins et al., "The interaction properties of costimulatory molecules revisited," Immunity, vol. 17, pp. 201-210, 2002.

Griesser, "The Importance of Solvates," Polymorphism in the Pharmacuetical Industry, Chapter 8, pp. 211-230, 2006.

Huxley et al., "High-affinity small molecule inhibitors of T cell costimulation," Chem. Biol., vol. 11, pp. 1651-1658, 2004.

Kobata et al., "Role of costimulatory molecules in autoimmunity," Rev. Immunogenet. 2, 74-80, 2000.

Lenschow et al., "CD28/B7 system of T cell costimulation," Annu. Rev. Immunol., vol. 14, pp. 233-258, 1996.

Lukes et al., "Oral feeding with pig peripheral lymphocytes decreases the xenogeneic delayed type hypersensitivity reaction in galactosyltransferase knockout mice," Abstract, Transplant Proc., vol. 37, No. 8, pp. 3327-3331, 2005.

MediGene, http://www.medigene.de/englisch/ProjektRH.php, download, Oct. 9, 2009.

Morris, "Structural Aspects of Hydrates and Solvates," Polymorphism in Pharmaceutical Solids, Chapter 4, No. 5, pp. 125-181, 1999.

Ninomiya et al., "Phosphorus in Organic Synthesis—VII," Tetrahedron, vol. 30, No. 4, pp. 2151-2157, 1974.

Saxena et al., "Abrogation of DTH response and mitogenic lectin- and alloantigen-induced activation of lymphocytes by calcium inhibitors TMB-8 and BAPTA-AM," Immunol. Lett., vol. 101, No. 1, pp. 60-64, Oct. 15, 2005.

Strieth et al., "Paclitaxel encapsulated in cationic liposomes increases tumor microvessel leakiness and improves therapeutic efficacy in combination with Cisplatin," Clin Cancer Res., vol. 14, No. 14, pp. 4603-4611, 2008.

Strieth et al., "Tumor-selective vessel occlusions by platelets after vascular targeting chemotherapy using paclitaxel encapsulated in cationic liposomes," Int J Cancer, vol. 122, No. 2, pp. 452-460, 2008.

Weiss et al., "CD8+ T cells in inflammatory demyelinating disease," J Neuroimmunol., vol. 191, Nos. 1-2, pp. 79-85, Nov. 2007.

Appel & Brossart, "Development of Novel Compounds to Treat Autoimmune and Inflammatory Diseases and Graft Versus Host Reactions," Endocrin. Metab. Immune Disord. Drug Targets 7, 93-97, 2007.

Brumeanu et al., "Down-regulation of autoreactive T-cells by HMG CoA reductase inhibitors," Clin. Immunol. 119, 1-12, 2006.

Chitale and Moots, "Abatacept: the first T lymphocyte co-stimulation modulator, for the treatment of rheumatoid arthritis," Expert. Opin. Biol. Ther. 2008; 8:115-122.

Choy, "T Cells in Psoriatic Arthritis," Curr. Rheumatol. Rep. 6, 437-41, 2007.

Cope et al., "The central role of T cells in rheumatoid arthritis," Clin. Exp. Rheumatol. 24, 4-11, 2007.

Dubey et al., "Costimulatory requirements of naive CD4+ T cells. ICAM-1 or B7-1 can costimulate Naïve CD4 T Cell Activation but Both Are Required for Optimum Response," J Immunol.1995; 155: 45-57.

Gimmi et al., "Human T-cell clonal anergy is induced by antigen presentation in the absence of B7 costimulation," Proc. Nat. Acad. Sci. USA 90, pp. 6586-6590, Jul. 1993.

Kristensen et al., "The number needed to treat for adalimumab, etanercept, and infliximab based on ACR50 response in three randomized controlled trials on established rheumatoid arthritis: a systematic literature review," Scand. J. Rheumatol. 2007; 36:411-417.

Linsley et al., "Binding of the B Cell Activation Antigen B7 to CD28 Costimulates T Cell Proliferation and Interleukin 2 mRNA Accumulation," J. Exp. Med. 173, 721-30, Mar. 1991.

Mallone & Endert, "T Cells in the Pathogenesis of Type 1 Diabetes," Curr. Diab. Rep. 8, 101-06, 2008.

Suresh et al., "Role of CD28-B7 Interactions in Generation and Maintenance of CD8 T Cell Memory," The Journal of Immunology, 2001, 167: 5565-5573.

Weiss et al., ."Role of CD28-B7 Interactions in Generation and Maintenance of CD8 T Cell Memory," Neuroimmunol. 191, 79-85, 2007.

Salomon, Benoit et al., B7/CD28 Costimulation Is Essential for the Homeostasis of the CD4+CD25 +Immunoregulatory T Cells That Control Autoimmune Diabetes, Immunity, vol. 12, pp. 431-440, dated Apr. 2000.

West, Anthony R., Solid State Chemistry and Its Applications, Wiley, New York, p. 365, dated 1988.

Database Beilstein 1992: BRN 343115, 325012, 361725, and 361896, entry dates 1988, citing J. Prakt. Chem. 2-121, p. 201 (1929); 5 pages.

Database Caplus Chemical Abstracts Service 1971, Database accession No. 74:87973, citing JP45026736B; 4 pages.

Database Beilstein 1992: BRN 269660 and 312421, entry date 1988, citing Michaelis, Justus Liebigs Ann. Chem. 373, p. 167 (1910); 2 pages.

* cited by examiner

IMMUNOMODULATING HETEROCYCLIC COMPOUNDS

This application is a divisional of U.S. Ser. No. 11/845,837 filed Aug. 28, 2007, now allowed, which is a divisional of U.S. Ser. No. 10/547,448, filed Jun. 20, 2006, now U.S. Pat. No. 7,276,505, issued Oct. 2, 2007, which case is a U.S. National Stage application of co-pending PCT application PCT/GB2004/001008 filed Mar. 10, 2004, which was published in English under PCT Article 21(2) on Sep. 23, 2004 under International Publication Number WO 2004/081011, and which claims the priority of Great Britain Patent Application No. 0305876.5, filed Mar. 14, 2003 and Great Britain Patent Application No. 0319429.7, filed Aug. 19, 2003. These applications are incorporated herein by reference in their entireties.

The present invention relates to novel heterocyclic compounds, to methods for their preparation, to compositions containing them, and to methods and use for clinical treatment of medical conditions which may benefit from immunomodulation, e.g. autoimmune disease, rheumatoid arthritis, multiple sclerosis, diabetes, asthma, transplantation, systemic lupus erythematosis and psoriasis. More particularly the present invention relates to novel heterocyclic compounds, which are CD80 antagonists capable of inhibiting the interactions between CD80 and CD28, useful for immunoinhibition.

BACKGROUND TO THE INVENTION

The immune system possesses the ability to control the homeostasis between the activation and inactivation of lymphocytes through various regulatory mechanisms during and after an immune response. Among these are mechanisms that specifically inhibit and/or turn off an immune response. Thus, when an antigen is presented by MHC molecules to the T-cell receptor, the T-cells become properly activated only in the presence of additional co-stimulatory signals. In the absence of these accessory signals there is no lymphocyte activation and either a state of functional inactivation termed anergy or tolerance is induced, or the T-cell is specifically deleted by apoptosis.

One such co-stimulatory signal involves interaction of CD80 on specialised antigen-presenting cells with CD28 on T-cells, and this signal has been demonstrated to be essential for full T-cell activation. (Lenschow et al. (1996) *Annu. Rev. Immunol.*, 14, 233-258). It would therefore be desirable to provide compounds which inhibit this CD80/CD28 interaction.

DETAILED DESCRIPTION OF THE INVENTION

According to the present invention there is provided a compound of formula (I) or a pharmaceutically or veterinarily acceptable salt, hydrate or solvate thereof:

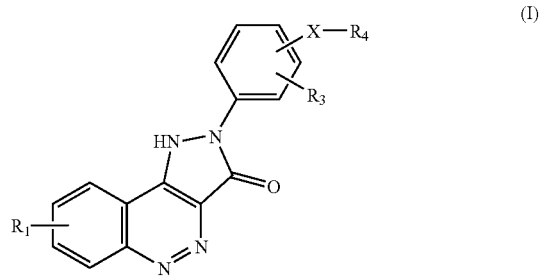

(I)

wherein
$R_1$ and $R_3$ independently represent H; F; Cl; Br; —$NO_2$; —CN; $C_1$-$C_6$ alkyl optionally substituted by F or Cl; or $C_1$-$C_6$ alkoxy optionally substituted by F;

$R_4$ represents a carboxylic acid group (—COOH) or an ester thereof, or —C(=O)$NR_6R_7$, —$NR_7$C(=O)$R_6$, —$NR_7$C(=O)$OR_6$, —NHC(=O)$NR_7R_6$ or —NHC(=S)$NR_7R_6$ wherein $R_6$ represents H, or a radical of formula -(Alk)$_m$-Q wherein m is 0 or 1
Alk is an optionally substituted divalent straight or branched $C_1$-$C_{12}$ alkylene, or $C_2$-$C_{12}$ alkenylene, or $C_2$-$C_{12}$ alkynylene radical or a divalent $C_3$-$C_{12}$ carbocyclic radical, any of which radicals may contain one or more —O—, —S— or —N($R_8$)— links wherein $R_8$ represents H or $C_1$-$C_4$ alkyl, $C_3$-$C_4$ alkenyl, $C_3$-$C_4$ alkynyl, or $C_3$-$C_6$ cycloalkyl, and
Q represents H; —$NR_9R_{10}$ wherein $R_9$ and $R_{10}$ independently represents H; $C_1$-$C_4$ alkyl; $C_3$-$C_4$ alkenyl; $C_3$-$C_4$ alkynyl; $C_3$-$C_6$ cycloalkyl; an ester group; an optionally substituted carbocyclic or heterocyclic group; or $R_9$ and $R_{10}$ form a ring when taken together with the nitrogen to which they are attached, which ring is optionally substituted; and
$R_7$ represents H or $C_1$-$C_6$ alkyl; or when taken together with the atom or atoms to which they are attached $R_6$ and $R_7$ form an optionally substituted monocyclic heterocyclic ring having 5, 6 or 7 ring atoms; and
X represents a bond or a divalent radical of formula —$(Z)_n$-(Alk)- or -(Alk)-$(Z)_n$— wherein Z represents —O—, —S— or —NH—, Alk is as defined in relation to $R_6$ and n is 0 or 1.

Compounds (I) may exist in the form of tautomers, such as ($I^1$) and ($I^2$):

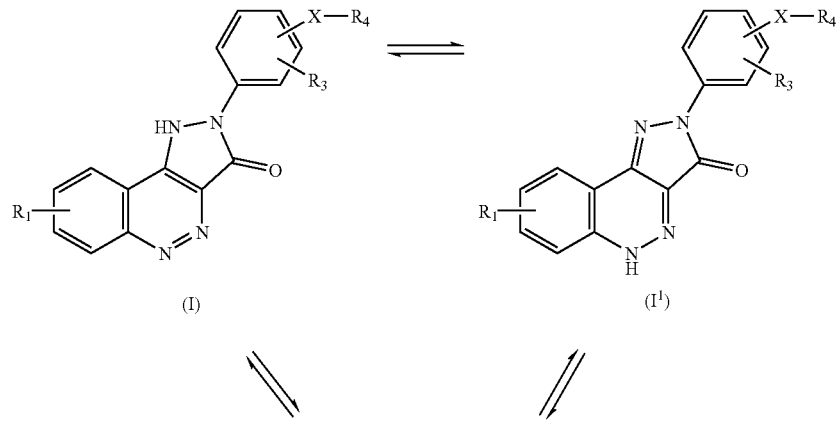

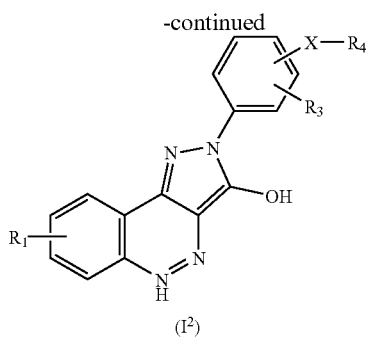

(I²)

Hereafter, the compounds of the invention may be represented and referred to in any tautomeric form (I), and it is to be understood that any and all tautomeric forms of structure (I), in particular (I¹) and (I²), are included in the invention.

Compounds of general formula (I) are CD80 antagonists. They inhibit the interaction between CD80 and CD28 and thus the activation of T cells, thereby modulating the immune response.

Accordingly the invention also includes:
(i) a compound of formula (I) or a pharmaceutically or veterinarily acceptable salt thereof for use in the treatment of conditions which benefit from immunomodulation, and in particular for immuno-inhibition.
(ii) the use of a compound of formula (I) or a pharmaceutically or veterinarily acceptable salt thereof in the manufacture of a medicament for the treatment of conditions which benefit from immunomodulation, and in particular for immuno-inhibition.
(iii) a method of immunomodulation, and in particular immuno-inhibition, in mammals, including humans, comprising administration to a mammal in need of such treatment an immunomodulatory effective dose of a compound of formula (I) or a pharmaceutically or veterinarily acceptable salt thereof.
(iv) a pharmaceutical or veterinary composition comprising a compound of formula (I) or a pharmaceutically or veterinarily acceptable salt thereof together with a pharmaceutically or veterinarily acceptable excipient or carrier.

Conditions which Benefit from Immunomodulation Include:
Acute disseminated encephalomyelitis
Adrenal insufficiency
Allergic angiitis and granulomatosis
Amylodosis
Ankylosing spondylitis
Asthma
Autoimmune Addison's disease
Autoimmune alopecia
Autoimmune chronic active hepatitis
Autoimmune haemolytic anaemia
Autoimmune Neutrogena
Autoimmune thrombocytopenic purpura
Behçet's disease
Cerebellar degeneration
Chronic active hepatitis
Chronic inflammatory demyelinating polyradiculoneuropathy
Chronic neuropathy with monoclonal gammopathy
Classic polyarteritis nodosa
Congenital adrenal hyperplasia
Cryopathies
Dermatitis herpetiformis
Diabetes
Eaton-Lambert myasthenic syndrome
Encephalomyelitis
Epidermolysis bullosa acquisita
Erythema nodosa
Gluten-sensitive enteropathy
Goodpasture's syndrome
Guillain-Barre syndrome
Hashimoto's thyroiditis
Hyperthyroidism
Idiopathic hemachromatosis
Idiopathic membranous glomerulonephritis
Isolated vasculitis of the central nervous system
Kawasaki's disease
Minimal change renal disease
Miscellaneous vasculitides
Mixed connective tissue disease
Multifocal motor neuropathy with conduction block
Multiple sclerosis
Myasthenia gravis
Opsoclonus-myoclonus syndrome
Pemphigoid
Pemphigus
pernicious anaemia
Polymyositis/dermatomyositis
Post-infective arthritides
Primary biliary sclerosis
Psoriasis
Reactive arthritides
Reiter's disease
Retinopathy
Rheumatoid arthritis
Sclerosing cholangitis
Sjögren's syndrome
Stiff-man syndrome
Subacute thyroiditis
Systemic lupus erythematosis
Systemic necrotizing vasculitides
Systemic sclerosis (scleroderma)
Takayasu's arteritis
Temporal arteritis
Thromboangiitis obliterans
Type I and type II autoimmune polyglandular syndrome
Ulcerative colitis
Uveitis
Wegener's granulomatosis As used herein, the term "ester" refers to a group of the form —COOR, wherein R is a radical notionally derived from the alcohol ROH. Examples of ester groups include the physiologically hydrolysable esters such as the methyl, ethyl, n- and iso-propyl, n-, sec- and tert-butyl, and benzyl esters.

As used herein the term "alkylene" refers to a straight or branched alkyl chain having two unsatisfied valencies, for example —CH$_2$—, —CH$_2$CH$_2$—, —CH$_2$CH$_2$CH$_2$—, —CH(CH$_3$)CH$_2$—, —CH(CH$_2$CH$_3$)CH$_2$CH$_2$CH$_2$—, and —C(CH$_3$)$_3$.

As used herein the term "alkenylene" refers to a straight or branched alkenyl chain having two unsatisfied valencies, for example —CH=CH—, —CH$_2$CH=CH—, —C(CH$_3$)=CH—, and —CH(CH$_2$CH$_3$)CH=CHCH$_2$—.

As used herein the term "alkynylene" refers to a straight or branched alkynyl chain having two unsatisfied valencies, for example —C≡C—, —CH$_2$C≡C—, and —CH(CH$_2$CH$_3$)C≡CCH$_2$—.

Unless otherwise specified in the context in which it occurs, the term "substituted" as applied to any moiety herein means substituted with at least one substituent, selected from, for example, (C$_1$-C$_6$)alkyl, (C$_1$-C$_6$)alkenyl, (C$_2$-C$_6$)alkynyl, fluoro-substituted (C$_1$-C$_6$)alkyl, fluoro-substituted (C$_1$-C$_6$)alkenyl, fluoro-substituted (C$_2$-C$_6$)alkynyl, (C$_1$-C$_6$)alkoxy and fluoro-substituted (C$_1$-C$_6$)alkoxy (including the special case where a ring is substituted on adjacent ring C atoms by alkylenedioxy such as methylenedioxy or ethylenedioxy), (C$_1$-C$_6$)alkylthio, phenyl, benzyl, phenoxy, benzyloxy, hydroxy, mercapto, amino, fluoro, chloro, bromo, cyano, nitro, oxo, —COOH, —SO$_2$OH, —CONH$_2$, —SO$_2$NH$_2$, —COR$^A$, —COOR$^A$, —SO$_2$OR$^A$, —NHCOR$^A$, —NHSO$_2$R$^A$, —CONHR$^A$, —SO$_2$NHR$^A$, —NHR$^A$, —NR$^A$R$^B$, —CONR$^A$R$^B$ or —SO$_2$NR$^A$R$^B$ wherein R$^A$ and R$^B$ are independently a (C$_1$-C$_6$)alkyl or (C$_2$-C$_6$)alkoxy group or a monocyclic carbocyclic or heterocyclic group of from 5-7 ring members, or R$^A$ and R$^B$ form a ring when taken together with the nitrogen to which they are attached. In the case where "substituted" means substituted by phenyl, benzyl, phenoxy, or benzyloxy, the phenyl ring thereof may itself be substituted with any of the foregoing, except phenyl, benzyl, phenoxy, or benzyloxy.

As used herein the term "aryl" refers to a mono-, bi- or tri-cyclic carbocyclic aromatic radical, and to two such radicals covalently linked to each other, Illustrative of such radicals are phenyl, biphenyl and napthyl.

As used herein the unqualified term "carbocyclyl" or "carbocyclic" includes aryl, cycloalkyl and cycloalkenyl and refers to a ring system (monocyclic, bicyclic, tricyclic or bridged) whose ring atoms are all carbon.

As used herein the unqualified term "cycloalkyl" refers to a carbocyclic ring system which contains only single bonds between ring carbons.

As used herein the unqualified term "cycloalkenyl" refers to a carbocyclic ring system which contains at least one double bond between a pair of ring carbons.

As used herein the term "heteroaryl" refers to a mono-, bi- or tri-cyclic aromatic radical containing one or more heteroatoms selected from S, N and O. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in particular means a mono-, bi- or tri-cyclic or bridged non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, tetrahydrofuranyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, tetrahydropyranyl, quinuclidinyl, isoxazolyl, benzimidazolyl, methylenedioxyphenyl, ethylenedioxyphenyl, maleimido and succinimido groups.

Some compounds of the invention contain one or more chiral centres because of the presence of asymmetric carbon atoms. The presence of asymmetric carbon atoms gives rise to stereoisomers or diastereoisomers with R or S stereochemistry at each chiral centre. The invention includes all such stereoisomers and diastereoisomers and mixtures thereof.

Salts of salt forming compounds of the invention include physiologically acceptable acid addition salts and base salts Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Methods

Compounds of the invention wherein R$_4$ represents an amide group —C(=O)NR$_6$R$_7$ may be prepared by reaction of the appropriate amine HNR$_6$R$_7$ with a compound of formula (II) to amidate the carboxylic acid group:

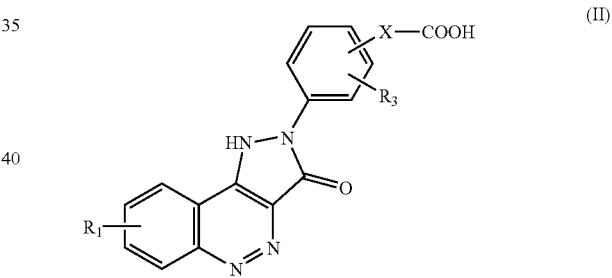

(II)

the symbols R$_1$, R$_3$, X, R$_6$ and R$_7$ being as defined in relation to formula (I) above.

Compounds (II) (ie compounds (I) of the invention wherein R$_4$ is a carboxylic acid group) may be prepared by reaction of a compound of formula (III) with a hydrazine of formula (IV):

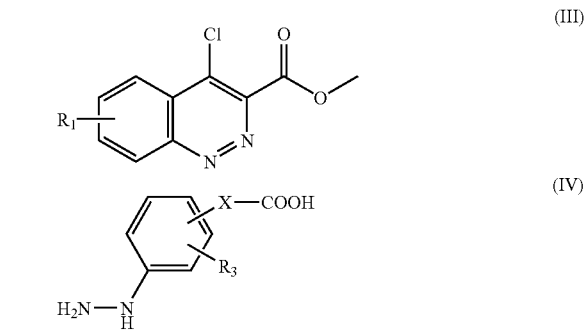

(III)

(IV)

This reaction may result in the preparation of a mixture of the position isomers (IIA) and (IIB):

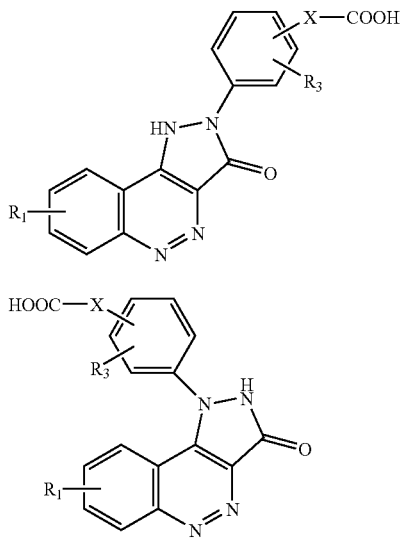

from which the desired isomer (IIA) may be separated.

Compounds (I) wherein $R_4$ is an ester or amide group may also be prepared from intermediate (III) by reaction with the appropriate hydrazine (IVA)

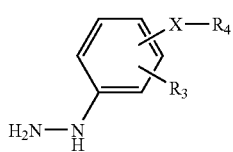

wherein $R_4$ is an ester or amide group. Again the reaction may result in a mixture of the ester or amide analogues of the carboxylic acids (IIA) and (IIB), from which the desired ester or amide isomer (I) may be separated. Alternatively, the carboxylic acid compound (II) may simply be esterified, or amidated.

Compounds (I) wherein $R_4$ is a "reverse amide" group —$NR_7C(=O)R_6$ may be prepared by Curtius rearrangement (see Ninomiya, K.; Shioiri, T.; Yamada, S. Tetrahedron (1974), 30(14), 2151-7) of the carboxylic acid (II) to the isocyanate (V)

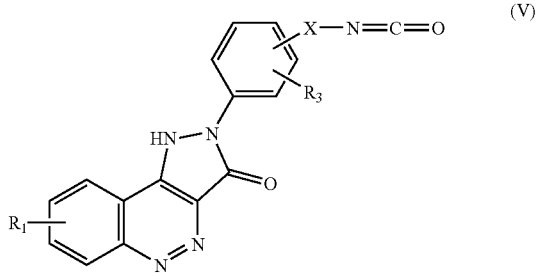

followed by hydrolysis of the isocyanate group to an amino group and acylation of the amino group with, for example, the acid chloride Cl—$C(=O)R_6$. In cases where $R_7$ is not hydrogen, the $R_7$ substituent may be introduced after the isocyanate reduction step or after the acylation step.

In an alternative route to the "reverse amide" ($R_4$=—$NR_7C(=O)R_6$) compounds of the invention, a compound of structure (V) in which the isocyanate moiety is replaced by a nitro group may be reduced to the corresponding amine, which may then be acylated to form the desired reverse amide.

Compounds (I) wherein $R_4$ is a urea group —$NHC(=O)NHR_6$ or thiourea group —$NHC(=S)NHR_6$ may also be prepared from the isocyanate (V) or the corresponding isothiocyanate by reaction with the appropriate amine $H_2NR_6$.

Compounds (I) wherein $R_4$ is a carbamate group —$NR_7C(=O)OR_6$ may be prepared by the reaction of the isocyanate with an appropriate alcohol $R_6OH$.

Further details of the synthetic methods for the preparation of compounds (I) of the invention, and intermediates such as (III), may be found in the examples herein.

In the compounds of the invention:

The radical $R_4X$— is preferably in the 4-position of the phenyl ring.

X may be, for example a bond, or a —$CH_2$— or —$CH_2CH_2$— radical. A bond is presently preferred.

$R_3$ may be, for example, H, F, Cl, methyl, methoxy, or methylenedioxy. Currently it is preferred that $R_3$ is H.

$R_1$, may be, for example, H, F, Cl, methyl, methoxy, or methylenedioxy. Currently it is preferred that $R_1$, be hydrogen or fluoro, particularly in the 6-position of the 3-oxo-1,3-dihydro-2H-pyrazolo[4,3-c]cinnolin-2-yl ring system.

$R_4$ represents a carboxylic acid group (—COOH) or an ester thereof, or —$C(=O)NR_6R_7$, —$NR_7C(=O)R_6$, —$NR_7C(=O)OR_6$ or —$NHC(=O)NHR_6$, all as defined above.

When $R_4$ is an ester group, examples include those of formula —COOR wherein R is methyl, ethyl n- or iso-propyl, n-, sec- or tert-butyl, or benzyl ester.

$R_6$, when present, represents H, or a radical of formula -(Alk)$_m$-Q wherein m, Alk and Q being as defined above. When m is 1, Alk may be, for example a straight or branched $C_1$-$C_6$ alkylene radical, such as —$CH_2$—, —$CH_2CH_2$—, —$CH_2CH_2CH_2$—, and —$CH_2CH(CH_3)CH_2$—. Alk may also be, for example, a divalent cyclopropylene, cyclopentylene or cyclohexylene radical. The radical Alk may be optionally substituted by, for example, OH, oxo, $CF_3$, methoxy or ethoxy. The radical Alk may optionally contain a hetero atom, for example in the form of an ether, thioether or amino linkage.

The group Q may represent, for example, hydrogen; —$NR_9R_{10}$ wherein $R_9$ and $R_{10}$ may be the same or different and selected from hydrogen, methyl, ethyl, n- or isopropyl or tert-butyl; an ester group for example a methyl, ethyl or benzyl ester; or an optionally substituted aryl, aryloxy, cycloalkyl, cycloalkenyl or heterocyclic group, for example phenyl, phenoxy, cyclopentyl, cyclohexyl, furyl, thienyl, quinuclidinyl, piperidyl, or piperazinyl group.

$R_7$ when present represents H or $C_1$-$C_6$ alkyl, for example methyl, ethyl n- or iso-propyl, n-, sec- or tert-butyl; or when taken together with the atom or atoms to which they are attached $R_6$ and $R_7$ form a monocyclic heterocyclic ring having 5, 6 or 7 ring atoms.

Especially preferred are the cases where $R_4$ represents —C(=O)NR$_6$R$_7$ or —NHC(=O)NR$_7$R$_6$ wherein $R_7$ is hydrogen and $R_6$ represents a radical of formula -(Alk)$_m$-Q wherein m is 1 and the divalent radical Alk contains 3 or 4 carbon atoms and is unsubstituted, and Q represents —NR$_9$R$_{10}$ wherein $R_9$ and $R_{10}$ independently represents H; $C_1$-$C_4$ alkyl; $C_3$-$C_4$ alkenyl; $C_3$-$C_4$ alkynyl; $C_3$-$C_6$ cycloalkyl; an ester group; an optionally substituted carbocyclic or heterocyclic group; or form a ring when taken together with the nitrogen to which they are attached, which ring is optionally substituted.

A specific preferred subset of compounds of the invention has formula (IC):

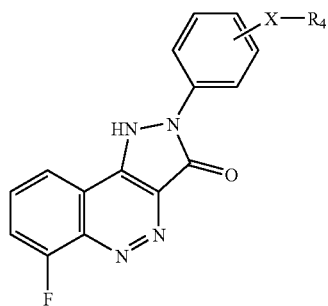

(IC)

wherein X and $R_4$ are as specified above. In this subset, the radical $R_4$X— may be in the 4-position of the phenyl ring. This subset includes in particular, compounds wherein X is a bond and $R_4$ is —C(=O)NR$_6$R$_7$ wherein $R_6$ and $R_7$ are as specified above. For example, in such compounds $R_6$ may be quinuclidinyl and $R_7$ hydrogen.

Specific compounds of the invention include those of the Examples herein.

A preferred compound of the invention is 4-(6-fluoro-3-oxo-1,3-dihydro-pyrazolo[4,3-c]cinnolin-2-yl)-N-(2,2-difluoro-ethyl)-benzamide, of formula (A)

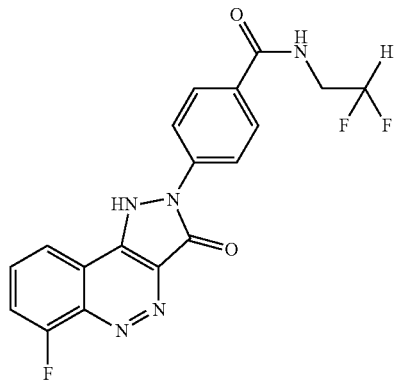

(A)

or a pharmaceutically or veterinarily acceptable salt, hydrate or solvate thereof.

Another preferred compound of the invention is N-[3-(tert-butyl-methyl-amino)-butyl]-4-(6-fluoro-3-oxo-1,3-dihydro-pyrazolo[4,3-c]cinnolin-2-yl)-benzamide, of formula (B):

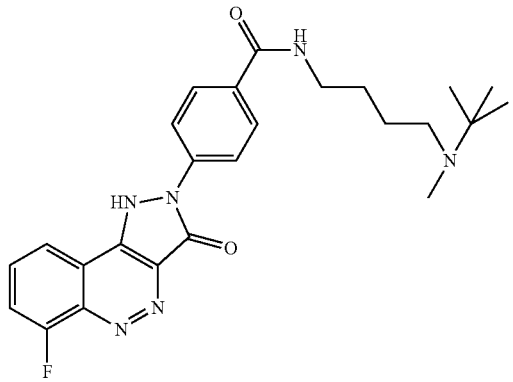

(B)

or a pharmaceutically or veterinarily acceptable salt, hydrate or solvate thereof.

As mentioned above, the invention includes pharmaceutical or veterinary composition comprising a compound of formula (I) or a pharmaceutically or veterinarily acceptable salt thereof together with a pharmaceutically or veterinarily acceptable excipient or carrier. In such compositions, it will be understood that the specific dose level for any particular patient will depend upon a variety of factors including the activity of the specific compound employed, the age, body weight, general health, sex, diet, time of administration, route of administration, rate of excretion, drug combination and the cause and severity of the particular disease undergoing therapy. Optimum dose levels and frequency of dosing will be determined by clinical trial.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

Embodiments of the invention are described in the following non-limiting Examples:

The following abbreviations are used in the experimental descriptions:

| DMF | Dimethyl formamide |
| DMA | Dimethyl acetamide |
| DMSO | Dimethyl sulphoxide |
| HBTU | O-Benzotriazol-1-yl-N,N,N',N'-tetramethyluronium hexafluorophosphate |
| HPLC | High performance liquid chromatography |
| LCMS | Liquid chromatography mass spectrum |
| NMR | Nuclear magnetic resonance spectroscopy |

Example 1

Step 1: Preparation of (phenylhydrazono)malonic acid

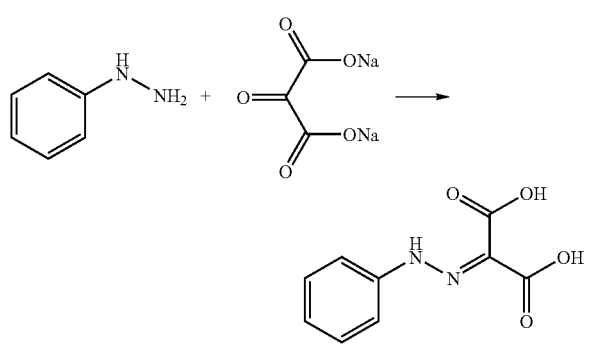

Sodium mesoxalate monohydrate (5.00 g, 27.8 mmol) was dissolved in 1 M hydrochloric acid (50 ml) to give a colourless cloudy solution. Phenylhydrazine (3.00 g, 2.72 ml, 27.8 mmol) was added dropwise at room temperature to the stirred mixture. A yellow precipitate formed, was collected by filtration after 90 min and washed with water (50 ml). The filter cake was triturated with ethyl acetate/hexane [1:1], filtered and dried under vacuum. The title compound was isolated as a yellow powder (4.74 g, 22.7 mmol, 82%). LCMS: m/z 207 [M–H]+.

Alternatively the product can be extracted from the aqueous phase with ethyl acetate (2×250 ml), the organic phase dried over magnesium sulphate, filtered and the solvent removed under vacuum.

Step 2: Preparation of (phenylhydrazono)malonoyl dichloride

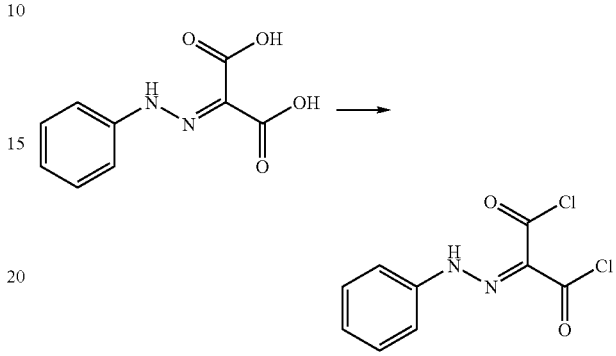

(Phenylhydrazono)malonic acid (1.00 g, 4.80 mmol) was mixed under inert atmosphere with dry chloroform (15 ml) to give a yellow suspension. The mixture was stirred at room temperature and phosphorus pentachloride (2.19 g, 10.5 mmol) was added portionwise. The reaction mixture was heated to reflux for 1.5 h to give a green solution. The mixture was cooled to room temperature and diluted with hexane (15 ml). A green precipitate formed, was collected by filtration and dried under vacuum. The title compound was isolated as a green powder (645 mg, 2.63 mmol, 53%).

Step 3: Preparation of methyl 4-hydroxycinnoline-3-carboxylate

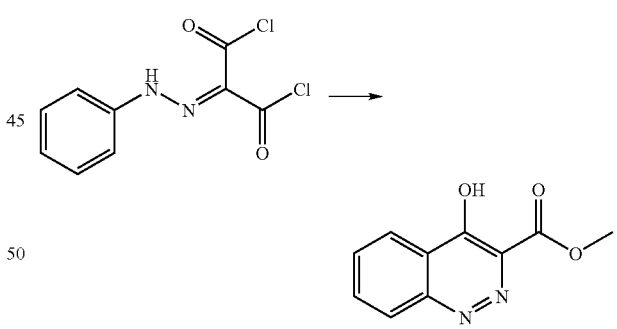

(Phenylhydrazono)malonoyl dichloride (2.45 g, 0.01 mmol) was mixed under inert atmosphere with 1,2-dichloroethane (15 ml) to give a yellow suspension. Titanium tetrachloride (1.89 g, 1.09 ml) was added dropwise to form a brown solution. The mixture was heated to reflux overnight, cooled to room temperature and quenched dropwise with methanol (15 ml). Stirring was continued for 30 min and volatiles were removed under vacuum. Water (100 ml) was added and the obtained suspension was extracted with n-butanol (2×50 ml). The combined organic phases were washed with water (2×20 ml) and concentrated under vacuum. The title compound was isolated as a green solid (1.04 g, 5.10 mmol, 51%). LCMS: m/z 205 [M+H]+.

Step 4: Preparation of methyl 4-chlorocinnoline-3-carboxylate

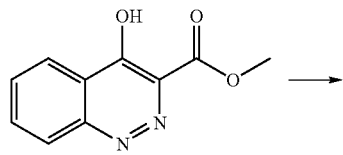

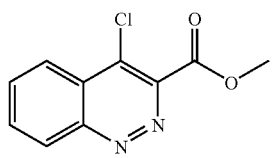

Thionyl chloride (8.15 g, 5 ml) was added dropwise under inert atmosphere to methyl 4-hydroxycinnoline-3-carboxylate (0.50 g, 2.45 mmol). The mixture was heated to reflux for 1.5 h, cooled to room temperature and excess thionyl chloride was removed under vacuum. Toluene (5 ml) was added to the residue. The mixture was stirred at room temperature overnight. The solids were collected by filtration and dried under vacuum. The title compound was isolated as a brown solid (248 mg, 1.11 mmol, 45%). LCMS: m/z 223 [M+H]$^+$.

Step 5: Preparation of 4-(3-oxo-1,3-dihydro-2H-pyrazolo[4,3-c]cinnolin-2-yl)benzoic acid

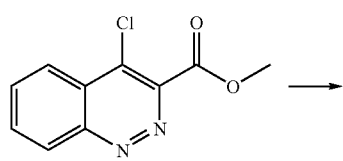

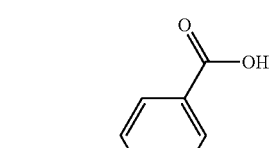

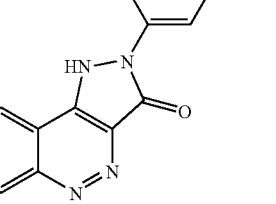

4-Hydrazinobenzoic acid (68.4 mg, 0.45 mmol) was mixed at room temperature with ethanol (5 ml) to give a crème-coloured suspension. Methyl 4-chlorocinnoline-3-carboxylate (100 mg, 0.45 mmol) was added and the mixture was heated to 45-50° C. for 1 h. The reaction mixture was cooled to room temperature and the solvent was removed under vacuum. Ethyl acetate (10 ml) was added to the residue. The mixture was stirred at room temperature for 1 h. The solids were collected by filtration and dried under vacuum. The title compound was isolated as a brown powder (120 mg, 0.39 mmol, 86%). LCMS: m/z 307 [M+H]$^+$. NMR [DMSO-d$_6$]: δ=7.69-7.77 (m, 1H$_{aryl}$); 7.81-7.90 (m, 2H$_{aryl}$); 8.05 (d, J=8.85, 2H$_{aryl}$); 8.20 (d, J=7.92 Hz, 1H$_{aryl}$); 8.33 (d, J=8.85 Hz, 2H$_{aryl}$); 14.64 (s, NH).

Alternatively the reaction may be carried out at room temperature. In this case, a longer reaction time of 2-3 h may be required.

Example 2

Preparation of N-[(dimethylamino)propyl]-4-(3-oxo-1,3-dihydro-2H-pyrazolo[4,3-c]cinnolin-2-yl)benzamide

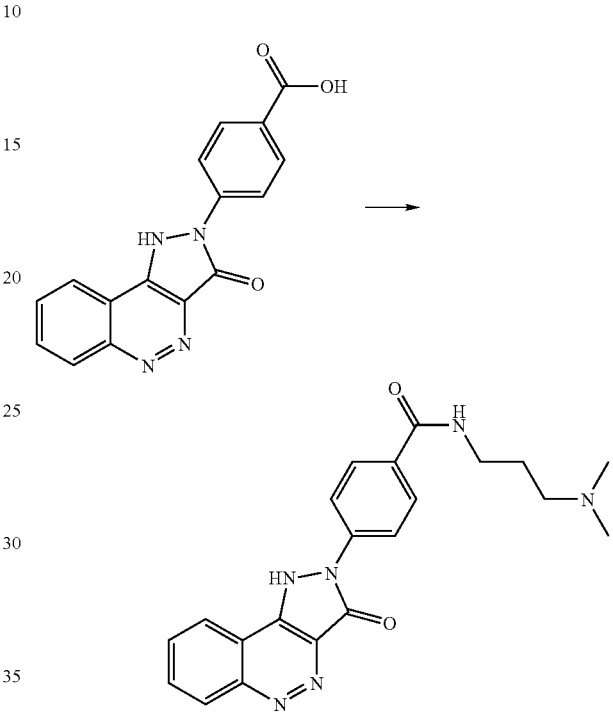

4-(3-oxo-1,3-dihydro-2H-pyrazolo[4,3-c]cinnolin-2-yl) benzoic acid (25 mg, 0.08 mmol) was mixed with DMF (1 ml). Diisopropylethylamine (21 mg, 28 µl, 0.16 mmol) and 3-dimethylaminopropylamine (8.2 mg, 10.0 µl, 0.09 mmol) were added followed by HBTU (30.3 mg, 0.08 mmol). The mixture was stirred at room temperature for 2 h. The product was purified by preparative HPLC. The title compound was isolated as a red solid (12.6 mg, 0.032 mmol, 40%). LCMS: m/z 391 [M+H]$^+$.

Example 3

Preparation of N-benzyl-4-(3-oxo-1,3-dihydro-2H-pyrazolo[4,3-c]cinnolin-2-yl)benzamide

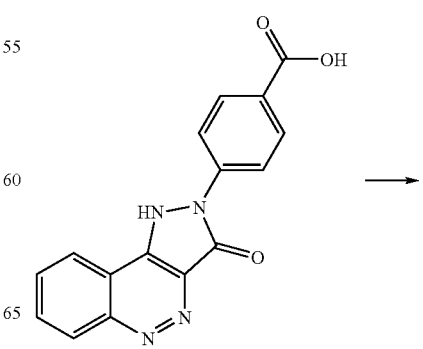

-continued

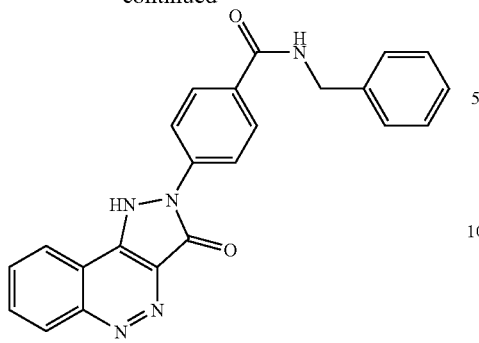

4-(3-oxo-1,3-dihydro-2H-pyrazolo[4,3-c]cinnolin-2-yl)benzoic acid (52 mg, 0.17 mmol) was mixed with DMF (2 ml). Diisopropylethylamine (22 mg, 29 μl, 0.17 mmol) and benzylamine (18.2 mg, 18.6 μl, 0.17 mmol) were added followed by HBTU (64.5 mg, 0.17 mmol). The mixture was stirred at room temperature for 4 h. The product was purified by preparative HPLC. The title compound was isolated as a red solid (6.6 mg, 0.02 mmol, 10%). LCMS: m/z 396 [M+H]$^+$.

Example 4

Step 1: Preparation of 4-(3-oxo-1,3-dihydro-2H-pyrazolo[4,3-c]cinnolin-2-yl)benzoyl chloride

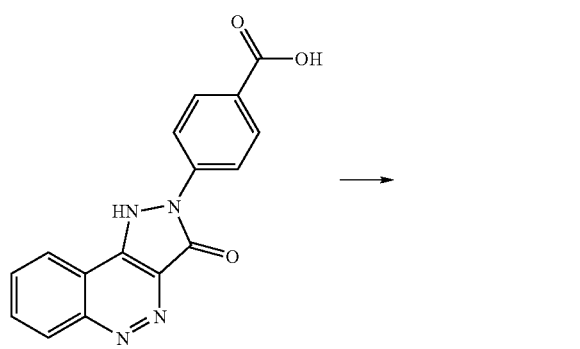

Thionyl chloride (90 ml) was added to 4-(3-oxo-1,3-dihydro-2H-pyrazolo-[4,3-c]cinnolin-2-yl)benzoic acid (2.36 g, 7.70 mmol). The mixture was heated to reflux for 2 h under nitrogen atmosphere. A dark red solution was obtained, cooled to room temperature and excess thionyl chloride was removed under vacuum. Toluene (30 ml) was added to the residues and the mixture was stirred at room temperature under nitrogen atmosphere until precipitation was complete. The solids were collected by filtration and washed with toluene (2×30 ml). The title compound was isolated as a red solid (2.20 g, 6.77 mmol, 88%) LCMS: m/z 321 [M+H]$^+$ (methyl ester resulting from sample make-up in methanol).

Step 2: Preparation of N-[(cyclohexylamino)propyl]-4-(3-oxo-1,3-dihydro-2H-pyrazolo[4,3-c]cinnolin-2-yl)benzamide

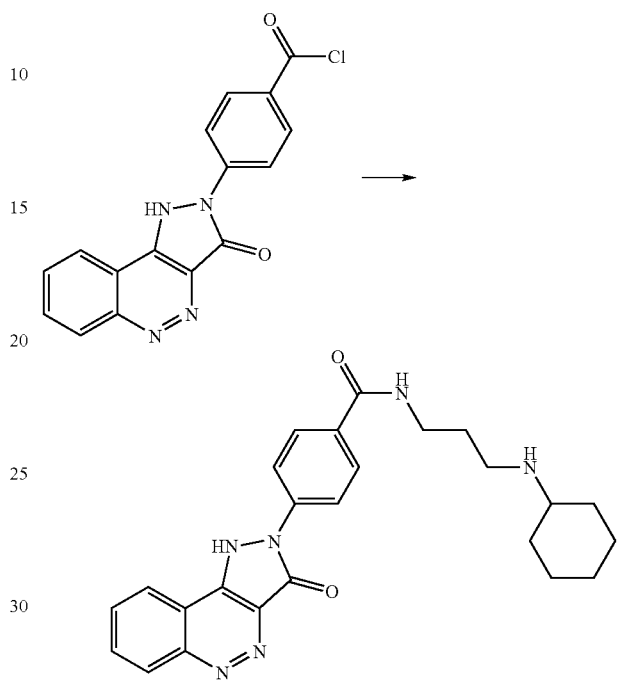

4-(3-oxo-1,3-dihydro-2H-pyrazolo[4,3-c]cinnolin-2-yl) benzoyl chloride (97 mg, 0.30 mmol) was dissolved in anhydrous DMA (2 ml). Diisopropylethylamine (39 mg, 53 μl, 0.60 mmol) was added followed by N-cyclohexyl-1,3-propanediamine (52 mg, 0.60 mmol). The mixture was stirred for 30 min. Water (5 ml) was added to give a dark red suspension. The mixture was extracted with n-butanol (2×20 ml). The combined organic phases were washed with water and concentrated under vacuum until precipitation was observed. Hexane (20 ml) and ethyl acetate (10 ml) were added, the solids were collected by filtration and dried under vacuum. The product was isolated as a dark red powder (82 mg, 0.18 mmol, 62%). LCMS: m/z 445 [M+H]$^+$.

Example 5

Step 1: Preparation of [(2-fluorophenyl)hydrazono]malonic acid

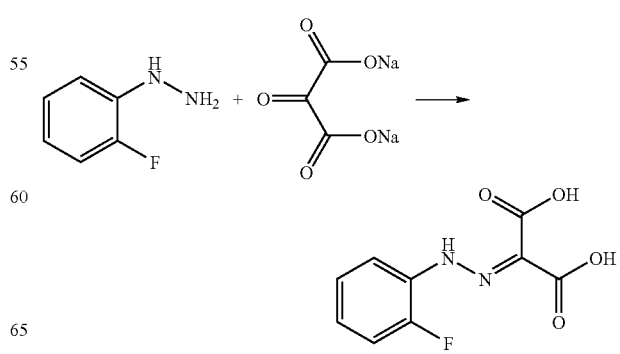

Sodium mesoxalate monohydrate (2.21 g, 12.3 mmol) was dissolved in 1 M hydrochloric acid (50 ml) to give a colourless cloudy solution. 2-Fluoro-phenylhydrazine hydrochloride (2.00 g, 12.3 mmol) was added portionwise at room temperature to the stirred mixture. A yellow precipitate formed, the mixture was diluted with water (50 ml) and stirring continued overnight. Ethyl acetate (150 ml) was added, the phases were mixed vigorously until the solids had dissolved. The phases were separated and the aqueous phase was washed with ethyl acetate (50 ml). The combined organic phases were dried over magnesium sulfate, filtered and the solvent removed under vacuum. The title compound was isolated as a yellow powder (2.55 g, 11.7 mmol, 92%). LCMS: m/z 227 [M−H]+.

Step 2: Preparation of [(2-fluorophenyl)hydrazono]malonoyl dichloride

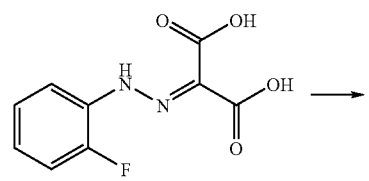

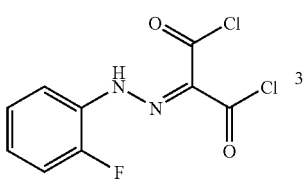

(2-Fluorophenylhydrazono)malonic acid (1.33 g, 5.88 mmol) was mixed under inert atmosphere with dry chloroform (20 ml) to give a yellow suspension. The mixture was stirred at room temperature and phosphorus pentachloride (2.69 g, 12.9 mmol) was added portionwise. The reaction mixture was heated to reflux for 2 h to give a dark yellow solution. The mixture was cooled to room temperature and concentrated under vacuum until precipitation occurred. The solids were collected by filtration, washed with hexane (30 ml) and dried under vacuum. The title compound was isolated as a yellow powder (760 mg, 2.89 mmol, 49%).

Step 3: Preparation of methyl 8-fluoro-4-hydroxycinnoline-3-carboxylate

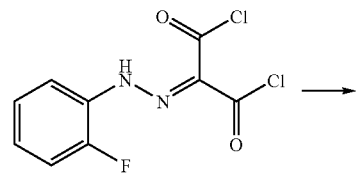

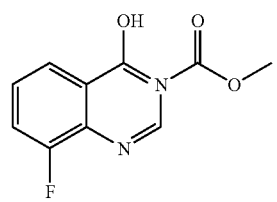

(2-Fluorophenylhydrazono)malonoyl dichloride (19.4 g, 74 mmol) was mixed under inert atmosphere with 1,2-dichloroethane (100 ml) to give a yellow suspension. Titanium tetrachloride (13.9 g, 8.08 ml, 74 mmol) was added dropwise to form a brown solution. The mixture was heated to reflux overnight. Further titanium tetrachloride (13.9 g, 8.08 ml, 74 mmol) was added and heating continued for 24 h. The reaction mixture was cooled to 0-5° C. and quenched dropwise with methanol (50 ml). Stirring was continued for 1 h at room temperature and volatiles were removed under vacuum. Water (300 ml) was added and the obtained suspension was extracted with ethyl acetate (3×100 ml). The combined organic phases were dried over magnesium sulphate, filtered and concentrated under vacuum. A yellow solid was obtained (12 g crude product). LCMS: m/z 223 [M+H]+.

Step 4: preparation of 4-(6-fluoro-3-oxo-1,3-dihydro-2H-pyrazolo[4,3-c]cinnolin-2-yl)benzoic acid

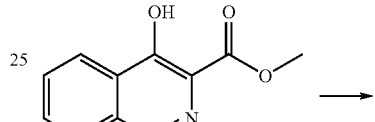

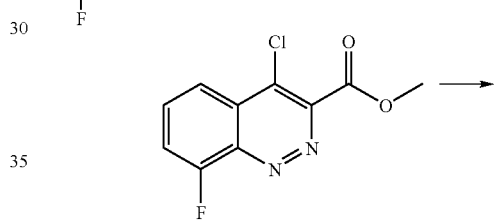

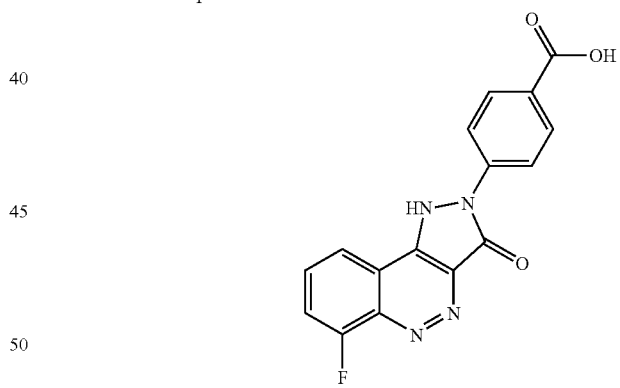

Crude 8-Fluoro-4-hydroxycinnoline-3-carboxylate from the previous stage (1.00 g, 4.95 mmol) was dissolved in thionyl chloride (50 ml). The solution was heated to reflux for 2-3 h until no further gas evolution was observed. The reaction mixture was cooled to room temperature and excess thionyl chloride was removed under vacuum. The crude intermediate was azeotroped with toluene (3×25 ml). A dark brown solid was obtained, which was taken up in ethanol (25 ml). 4-Hydrazinobenzoic acid (640 mg, 4.21 mmol) was added and the mixture was stirred at room temperature overnight. The solids were collected by filtration, slurried in 1 M HCl (100 ml), filtered, washed with hexane (50 ml) and dried under vacuum. A brown solid was obtained (890 mg of crude product). LCMS: m/z [M+H]+ 325.

Example 6

Step 1: Preparation of 4-(6-fluoro-3-oxo-1,3-dihydro-2H-pyrazolo[4,3-c]cinnolin-2-yl)benzoic acid chloride

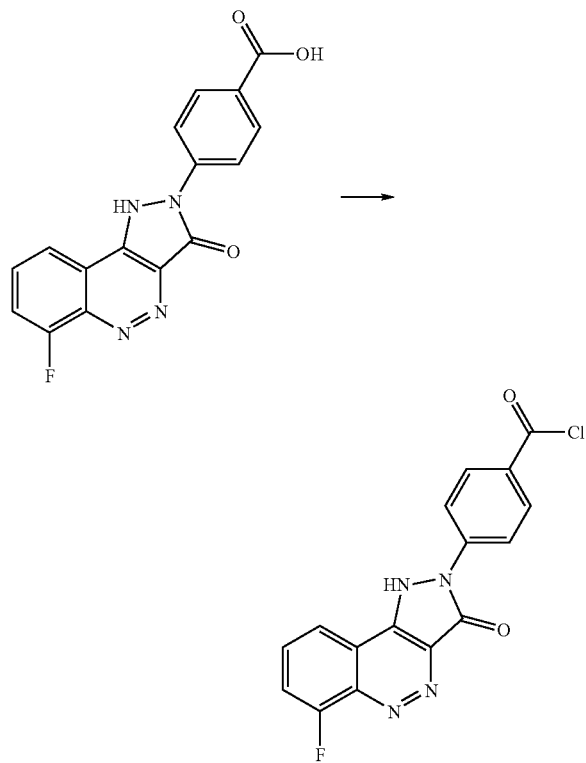

Crude 4-(6-fluoro-3-oxo-1,3-dihydro-2H-pyrazolo[4,3-c]cinnolin-2-yl)-benzoic acid (1.45 g) from the previous stage was dissolved in thionyl chloride (50 ml). The mixture was heated to 70° C. for 2-3 h until no further gas evolution was observed. The mixture was cooled to room temperature and excess thionyl chloride was removed under vacuum. The residues were azeotroped with toluene (2×20 ml) to give a solid. The solid was collected by filtration, washed with toluene and dried under vacuum. The product was isolated as a yellow powder (670 mg, 1.95 mmol). LCMS: m/z [M+H]+ 339 (methyl ester resulting from sample make-up in methanol).

Step 2: Preparation of 4-(6-fluoro-3-oxo-1,3-dihydro-2H-pyrazolo[4,3-c]cinnolin-2-yl)-N-(pyrrolidin-1-yl-butyl)benzamide

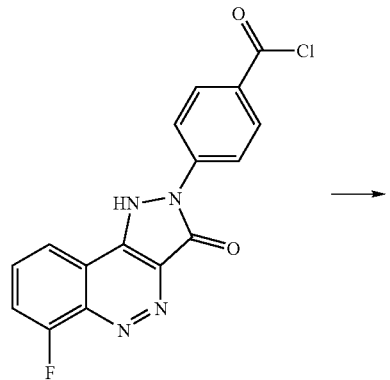

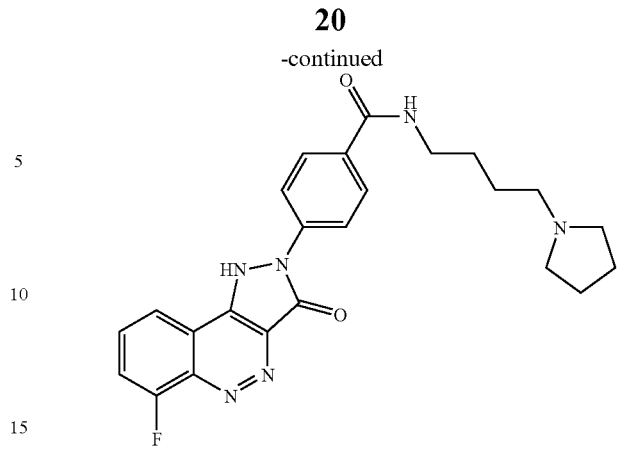

4-(6-fluoro-3-oxo-1,3-dihydro-2H-pyrazolo[4,3-c]cinnolin-2-yl)benzoyl chloride (100 mg, 0.29 mmol) was dissolved in anhydrous DMA (2 ml). Diisopropylethylamine (75 mg, 101 µl, 0.58 mmol) was added followed by 1-(4-aminobutyl)pyrrolidine (41 mg). The mixture was stirred at room temperature overnight. Water (5 ml) and n-butanol (5 ml) were added. The phases were separated. The organic phase was washed with water (2×5 ml). The volatiles were removed under vacuum. The product was isolated as a brown powder (50 mg, 0.11 mmol, 37%). LCMS: m/z [M+H]+ 463.

Example 7

Preparation of 4-(6-fluoro-3-oxo-1,3-dihydro-2H-pyrazolo[4,3-c]cinnolin-2-yl)-n-(1,2,2,6,6-pentamethylpiperidine-4-yl)benzamide

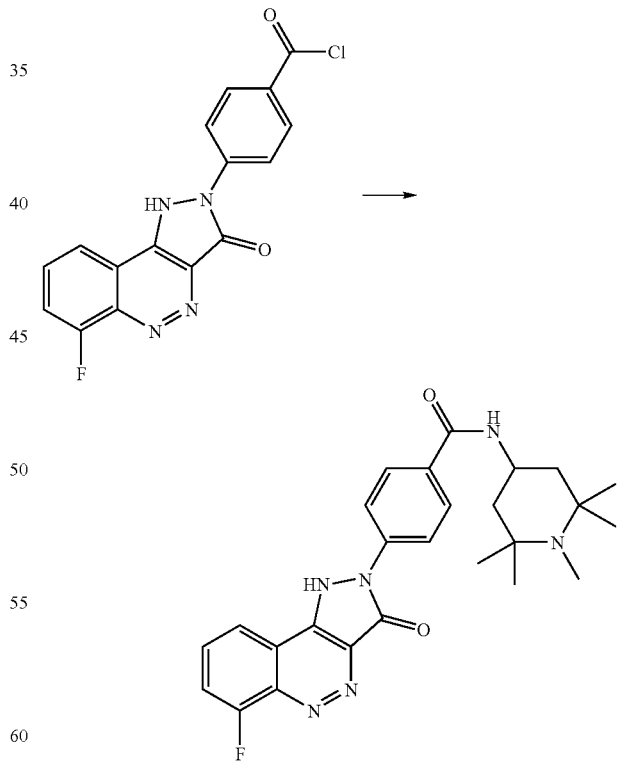

4-(6-fluoro-3-oxo-1,3-dihydro-2H-pyrazolo[4,3-c]cinnolin-2-yl)benzoyl chloride (100 mg, 0.29 mmol) was dissolved in anhydrous DMA (2 ml). Diisopropylethylamine (75 mg, 101 µl, 0.58 mmol) was added followed by 4-amino-1,2,2,6,6-pentamethylpiperidine (49 mg, 0.29 mmol). The mixture was stirred overnight. Water (5 ml) and n-butanol (5 ml) were added. The phases were separated. The organic phase was washed with water (2×5 ml) and the solution was concentrated under vacuum. The title compound was isolated as a dark red solid (50 mg, 0.105 mmol, 36%). LCMS: m/z [M+H]⁺ 477.

Example 8

Step 1: Preparation of 2-(4-nitrophenyl)-1,2-dihydro-3H-pyrazolo[4,3-c]cinnolin-3-one

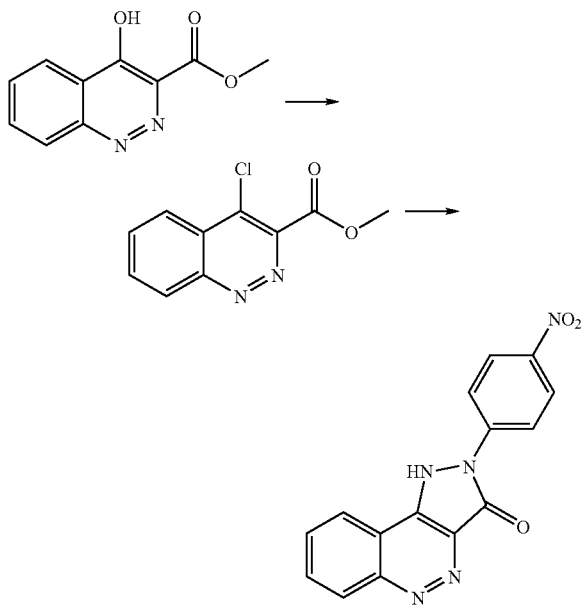

Thionyl chloride (326 g, 200 ml) was added dropwise under inert atmosphere to methyl 4-hydroxycinnoline-3-carboxylate (10.0 g, 49 mmol). The mixture was heated to reflux for 2.5 h, cooled to room temperature and excess thionyl chloride was removed under vacuum. Toluene (100 ml) was added to the residue and removed under vacuum. This procedure was repeated with further toluene (100 ml). A brown semi-solid material was obtained and taken up in ethanol (200 ml). 4-Nitrophenylhydrazine (5.99 g, 39.2 mmol) was added portionwise. The mixture was stirred at room temperature overnight. The mixture was heated to 40-45° C. for 1 h and cooled to room temperature. The solids were collected by filtration, triturated with ethanol (100 ml) and dried under vacuum. The title compound was isolated as a brown solid (8.42 g, 27.4 mmol, 70%). LCMS: m/z 308 [M+H]⁺.

Step 2: Preparation of 2-(4-aminophenyl)-1,2-dihydro-3H-pyrazolo[4,3-c]cinnolin-3-one

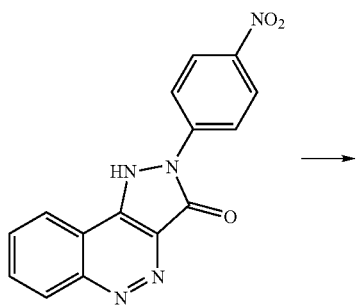

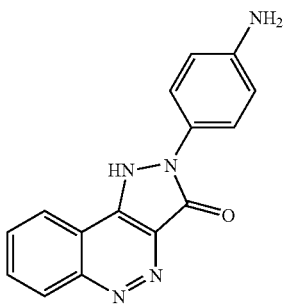

2-(4-nitrophenyl)-1,2-dihydro-3H-pyrazolo[4,3-c]cinnolin-3-one (11.4 g, 37.2 mmol) was suspended in a mixture of ethanol (100 ml) and water (100 ml). Iron powder (11.1 g, 200 mmol) and ammonium chloride (5.34 g, 100 mmol) were added. The mixture was heated to 80° C. overnight, cooled to room temperature and basified with potassium carbonate to pH 9-10. The solids were removed by filtration through a pad of Celite®. The filtrate was extracted with n-butanol (2×200 ml). The combined organic phases were concentrated under vacuum to give a dark red solid. The solid was triturated with methanol (100 ml), filtered and dried under vacuum. The title compound was isolated as a dark red powder (5.58 g, 20.1 mmol, 57%). LCMS: m/z 278 [M+H]⁺.

Step 3: Preparation of N-[3-(dimethylamino)propyl]-N'-[4-(3-oxo-1,3-dihydro-2H-pyrazolo[4,3-c]cinnolin-2-yl)phenyl]urea

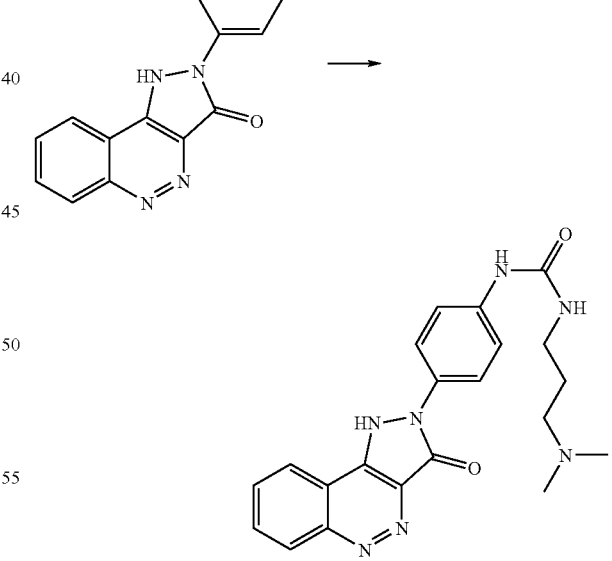

2-(4-aminophenyl)-1,2-dihydro-3H-pyrazolo[4,3-c]cinnolin-3-one (44 mg, 0.16 mmol) was suspended in toluene under nitrogen atmosphere (0.5 ml) at 0-5° C. DMA (0.5 ml) was added followed by N,N'-carbonyldiimidazole (26 mg, 0.16 mmol). The mixture was stirred for 1 h at 0-5° C. before mixed with a solution of 3-dimethylaminopropylamine (18 mg, 0.18 mmol) in toluene (0.5 ml). Stirring was continued for 1 h and the product was purified by preparative HPLC. The title compound was isolated as a dark red powder (2.6 mg, 6 µmol, 4%). LCMS: m/z 406 [M+H]⁺.

Example 9

Preparation of 4-(3-oxo-1,3-dihydro-2H-pyrazolo[4,3-c]cinnolin-2-yl)benzoic acid ethyl ester

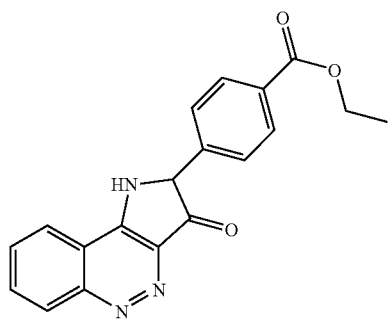

The title compound was prepared by the method of Example 1 step 5, substituting 4-hydrazinobenzoic acid ethyl ester for the parent acid. MS: MH+=335.2

Results

The Use of BIAcore Biomolecular Interaction Analysis

Biotinylated human CD80 (hCD80-BT) is a recombinant soluble form of a membrane bound receptor molecule (CD80) which binds to CD28 to initiate T cell activation. The interaction between CD80 and CD28 has been extensively investigated (Collins et al, 2002). Biotinlyated human HLA-A2-tax is the recombinant soluble form of a membrane bound receptor molecule that has been used in this example as a control protein, and is not expected to interact with the compounds.

The BIAcore S51™ system was used for screening the compounds of Examples 1-4 above. A series S sensor chip CM5 was docked onto the BIAcore S51™. Streptavidin was coupled to the carboxymethyl surface using standard amine coupling. The chip surface was activated with 0.2M EDC/0.05M NHS, followed by binding of streptavidin (0.25 mg/ml in 10 mM sodium acetate pH 5.0) and saturation of unoccupied sites with 1 M ethylenediamine.

The BIAcore S51 sensor chip has two separate sensor spots for immobilisation of proteins. hCD80-BT was immobilised on the streptavidin-coated surface of one sensor spot until a response of approximately 3000 RU was observed. A protein to control for non-specific binding of the compound was immobilised on a second sensor spot. The control protein used for these experiments was a biotinylated, soluble form of the human HLA protein.

Dilution series of compounds (1000 nM-0.05 nM) were prepared in running buffer (10 mM, pH 7.4, 150 mM NaCl, 0.005% P20; 5% DMSO).

BIAcore S51™ was run at a flow rate of 30 µl/min using running buffer. Compounds and DMSO standard solutions for correction of data for solvent effects were injected. Data were recorded automatically and were analysed using BIAcore S51 Evaluation software.

The interaction between CD80 and the endogenous protein ligand (CD28) is highly specific, but relatively weak, with a $K_D$ of 4750 nM, and an off-rate of greater than 0.2 s⁻¹. The compounds of Examples 2, 3, 4, 6, 7 have greater affinity and longer residence times on CD80 than CD28, having $K_D$S of less than 100 nM, and off-rates of 2×10⁻², indicating that the cinnolines will be able to compete effectively with the endogenous ligand. The cinnolines showed no detectable interaction with the control protein.

REFERENCES

Collins A V et al. (2002) Immunity 17, 201-210 "The interaction properties of costimulatory molecules revisited"

Inhibition of Production of Interleukin-2 (IL-2) by Human Jurkat T Cells.

Method

Human Raji cells were dispensed at a concentration of 2×10⁵ cells per well in RPMI-1640 medium supplemented with 10% fetal calf serum, 1% penicillin/streptomycin, 1% glutamine (RPMI medium) in a 96-well round bottom microtitre plate. Compounds under investigation (dissolved in 100% DMSO) were diluted to eight-fold the desired final concentration in RPMI medium and added to the required final concentration for a total volume of 200 µl per well. After 20 minutes incubation at 37° C., Jurkat T cells were added at a concentration of 2×10⁵ cells per well. Monoclonal antibody to CD3 (UCHT1, R&D Systems) was added to the cultures at a final concentration of 1 µg per ml, and where indicated, monoclonal antibody to CD28 (CD28.2, BD-Pharmingen) was also added at a concentration of 2.5 µg per ml. Cells were cultured at 37° C. for 5 hours, after which the plates were centrifuged and the supernatants harvested for IL-2 ELISA assay using the IL-2 Eli-pair kit (DIACLONE Research, Besancon, France) according to the manufacturers instructions.

By way of example, the compound of Example 2 (AV1142005) gave 65% inhibition at 30 µM.

Homogenous Time Resolved Fluorescence Assay

The examples described above were tested in a cell free Homogenous Time Resolved Fluorescence (HTRF) assay to determine their activity as inhibitors of the CD80-CD28 interaction.

In the assay, europium and allophycocyanin (APC) are associated with CD28 and CD80 indirectly (through antibody linkers) to form a complex, which brings the europium and APC into close proximity to generate a signal. The complex comprises the following six proteins: fluorescent label 1, linker antibody 1, CD28 fusion protein, CD80 fusion protein, linker antibody 2, and fluorescent label 2. The table below describes these reagents in greater detail.

| | |
|---|---|
| Fluorescent label 1 | Anti-Rabbit IgG labelled with Europium (1 µg/ml) |
| Linker antibody 1 | Rabbit IgG specific for mouse Fc fragment (3 µg/ml) |
| CD28 fusion protein | CD28 - mouse Fc fragment fusion protein (0.48 µg/ml) |
| CD80 fusion protein | CD80 mouse Fab fragment (C215) fusion protein (1.9 µg/ml) |
| Linker antibody 2 | GαMκ-biotin: biotinylated goat IgG specific for mouse kappa chain (2 µg/ml) |
| Fluorescent label 2 | SA-APC: streptavidin labelled allophycocyanin (8 µg/ml) |

On formation of the complex, europium and APC are brought into proximity and a signal is generated.

Non-specific interaction was measured by substituting a mouse Fab fragment (C215) for the CD80 mouse Fab fragment fusion protein (1.9 µg/ml). The assay was carried out in black 384 well plates in a final volume of 30 µl. Assay buffer: 50 mM Tris-HCl, 150 mM NaCl pH7.8, containing 0.1% BSA (w/v) added just prior to use.

Compounds were added to the above reagents in a concentration series ranging between 100 μM-1.7 nM. The reaction was incubated for 4 hours at room temperature. Dual measurements were made using a Wallac Victor 1420 Multilabel Counter. First measurement: excitation 340 nm, emission 665 nm, delay 50 μs, window time 200 μs. second measurement: excitation 340 nm, emission 615 nm, delay 50 μs, window time 200 μs. Counts were automatically corrected for fluorescence crossover, quenching and background. The EC50 activities of compounds tested are recorded as:

EC50:*=>10 μM,=1-10 μM,*=<1 μM.

The compounds of Examples 1-8 had the following activities in the HTRF assay described above:
Example 1 *
Example 2 ***
Example 3 ***
Example 4 ***
Example 5 *
Example 6 ***
Example 7 ***
Example 8 ***
Example 9 **

Additional Examples

Further examples of compounds of the invention were synthesised by methods analogous to those of Examples 1-8 above. The structures of the synthesised compounds are shown in the following Table, together with their activities in the HTRF assay described above.

TABLE

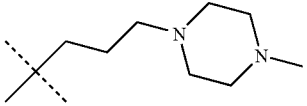

| Example No. | X | W | R | R' | MS MH+ | Activity |
|---|---|---|---|---|---|---|
| 9a. | H | — | CH₂CH₂OMe | H | 364.2 | ** |
| 10. | H | — | 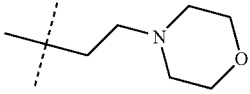 | H | 446.2 | *** |
| 11. | H | — | CH₂CH₂NMe₂ | H | 377.1 | *** |
| 12. | H | — | 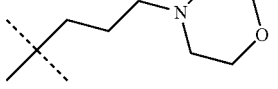 | H | 419.1 | *** |
| 13. | H | — | 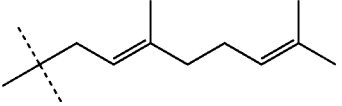 | H | 433.1 | *** |
| 14. | H | — | 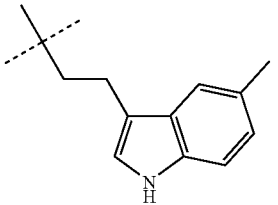 | H | 442.0 | * |
| 15. | H | — | Ph | H | 382.0 | ** |
| 16. | H | — | (5-methylindol-3-yl)ethyl | H | 463.0 | * |

TABLE-continued
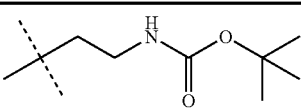
| Example No. | X | W | R | R' | MS MH+ | Activity |
|---|---|---|---|---|---|---|
| 17. | H | — | 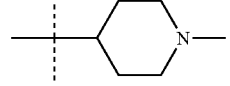 | H | 448.8 | ** |
| 18. | H | — | 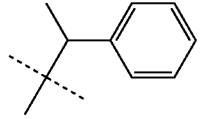 | H | 403.1 | *** |
| 19. | H | — | 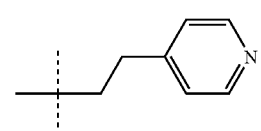 | H | 410.0 | * |
| 20. | H | — | 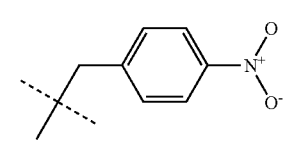 | H | 411.0 | *** |
| 21. | H | — | 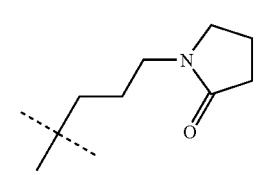 | H | 441.2 | ** |
| 22. | H | — | 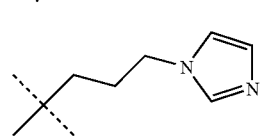 | H | 431.1 | ** |
| 23. | H | — | 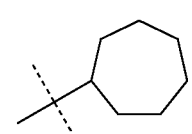 | H | 414.1 | *** |
| 24. | H | — | 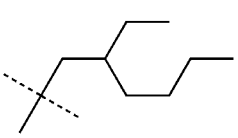 | H | 402.2 | ** |
| 25. | H | — |  | H | 418.4 | * |

TABLE-continued

| Example No. | X | W | R | R' | MS MH+ | Activity |
|---|---|---|---|---|---|---|
| 26. | H | — | (3,7-dimethyloctyl) | H | 418.2 | *** |
| 27. | H | — | (2-methyloctyl) | H | 418.2 | * |
| 28. | H | — | (methacrylate ester chain) | H | 417.9 | ** |
| 29. | H | — | (4-hydroxypentyl, gem-dimethyl) | H | 378.0 | *** |
| 30. | H | — | (cyclohexylaminobutyl, gem-dimethyl) | H | 445.2 | *** |
| 31. | H | — | (5-methoxyindol-3-yl-propyl, gem-dimethyl) | H | 479.0 | ** |
| 32. | H | — | (2-methylpiperidin-1-yl-propyl, gem-dimethyl) | H | 445.2 | *** |
| 33. | H | — | (2,3-dimethylbutyl, gem-dimethyl) | H | 376.2 | ** |
| 34. | H | — | (ethyl 3-methylbutanoate, gem-dimethyl) | H | 420.0 | ** |

TABLE-continued
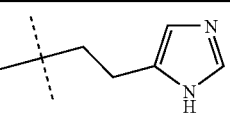
| Example No. | X | W | R | R' | MS MH+ | Activity |
|---|---|---|---|---|---|---|
| 35. | H | — | 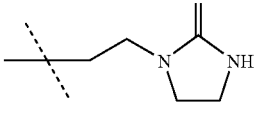 | H | 400.0 | ** |
| 36. | H | — | 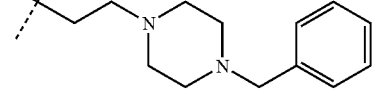 | H | 418.0 | * |
| 37. | H | — | 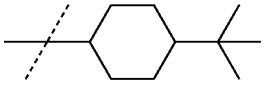 | H | 508.1 | *** |
| 38. | H | — | 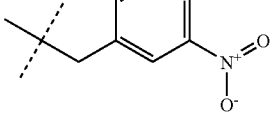 | H | 444.2 | * |
| 39. | H | — | 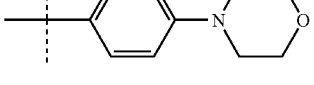 | H | 441.1 | ** |
| 40. | H | — | 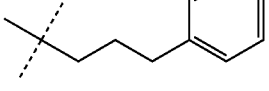 | H | 467.2 | ** |
| 41. | H | — | 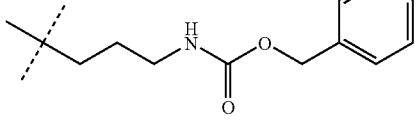 | H | 424.1 | ** |
| 42. | H | — | 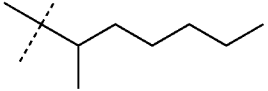 | H | 496.9 | ** |
| 43. | H | — | | H | 404.1 | ** |

TABLE-continued
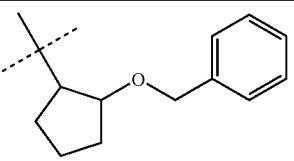
| Example No. | X | W | R | R' | MS MH+ | Activity |
|---|---|---|---|---|---|---|
| 44. | H | — | 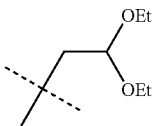 | H | 480.0 | * |
| 45. | H | — | 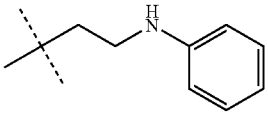 | H | 421.8 | ** |
| 46. | H | — | Et | H | 334.2 | *** |
| 47. | H | — | 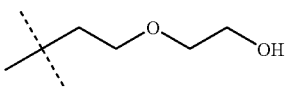 | H | 425.0 | *** |
| 48. | H | — | CH$_2$CH$_2$NHMe | H | 363.0 | *** |
| 49. | H | — | CH$_2$CH$_2$NHEt | H | 377.1 | *** |
| 50. | H | — | 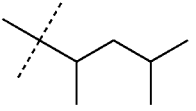 | H | 394.2 | ** |
| 51. | H | — | CH$_2$CH$_2$OH | H | 350.2 | *** |
| 52. | H | — | CH$_2$CH$_2$NHMe | H | 377.2 | *** |
| 53. | H | — | CH$_2$CH$_2$CH$_2$OiPr | H | 406.2 | *** |
| 54. | H | — | CH$_2$CH$_2$CH$_2$CH$_2$NH$_2$ | H | 377.2 | *** |
| 55. | H | — | 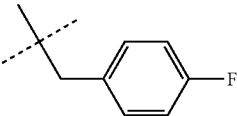 | H | 390.2 | *** |
| 56. | H | — | 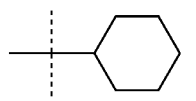 | H | 414.1 | ** |
| 57. | H | — |  | H | 388.2 | ** |
| 58. | H | — | CH$_2$CH$_2$CH$_2$N(nBu)$_2$ | H | 475.2 | *** |
| 59. | H | — | cyclododecyl | H | 472.2 | * |
| 60. | H | — | CH$_2$CH$_2$NEt$_2$ | H | 405.1 | *** |

TABLE-continued
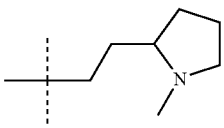
| Example No. | X | W | R | R' | MS MH+ | Activity |
|---|---|---|---|---|---|---|
| 61. | H | — | 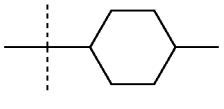 | H | 417.2 | *** |
| 62. | H | — | 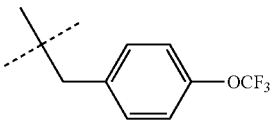 | H | 402.2 | ** |
| 63. | H | — | CH$_2$CH$_2$OPh | H | 426.0 | ** |
| 64. | H | — | 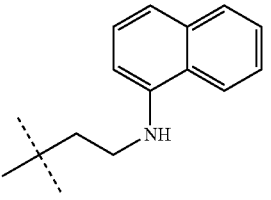 | H | 480.2 | ** |
| 65. | H | — | 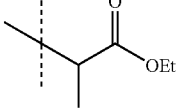 | H | 475.2 | ** |
| 66. | H | — | 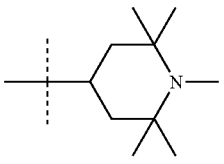 | H | 406.1 | ** |
| 67. | H | — | CH$_2$CH$_2$CH$_2$OnBu | H | 420.0 | *** |
| 68. | H | — | 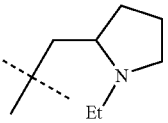 | H | 459.3 | *** |
| 69. | H | — |  | H | 417.3 | *** |

TABLE-continued

| Example No. | X | W | R | R' | MS MH+ | Activity |
|---|---|---|---|---|---|---|
| 70. | H | — | *sec-butyl-methyl (R isomer)* | H | 362.3 | *** |
| 71. | H | — | *sec-butyl-methyl (S isomer)* | H | 362.3 | *** |
| 72. | H | — | $CH(Et)_2$ | H | 376.3 | ** |
| 73. | H | — | $CH_2CH_2CH_2CH_2Ph$ | H | 438.4 | ** |
| 74. | H | — | *CH(CH_2CH_2CO_2Et)(CO_2Et)* | H | 492.2 | ** |
| 75. | H | — | *1-cyclohexylethyl-methyl* | H | 416.3 | ** |
| 76. | H | — | *2-(pyridin-2-yl)ethyl-methyl* | H | 411.2 | ** |
| 77. | H | — | $CH_2CH_2SEt$ | H | 394.2 | *** |
| 78. | H | — | Cyclopropyl | H | 346.2 | ** |
| 79. | H | — | *3-(pyrrolidin-1-yl)propyl* | H | 417.3 | *** |
| 80. | H | — | *1-benzylpiperidin-3-yl* | H | 479.3 | *** |

TABLE-continued
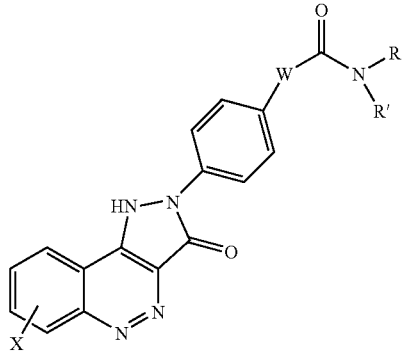
| Example No. | X | W | R | R' | MS MH+ | Activity |
|---|---|---|---|---|---|---|
| 81. | H | — | 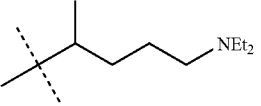 | H | 447.2 | *** |
| 82. | H | — | CH₂CH₂CH(CH₃)CH₃ | H | 376.2 | ** |
| 83. | H | — | cyclopentyl | H | 374.2 | ** |
| 84. | H | — | nPropyl | H | 348.2 | ** |
| 85. | H | — | CH₂CH₂tBu | H | 390.3 | ** |
| 86. | H | — | 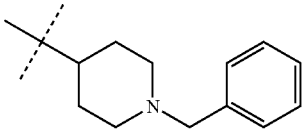 | H | 479.3 | *** |
| 87. | H | — | CH₂cycloheptyl | H | 416.4 | * |
| 88. | H | — | 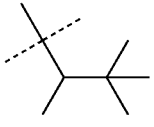 | H | 390.3 | ** |
| 89. | H | — | 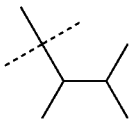 | H | 376.3 | *** |
| 90. | H | — | 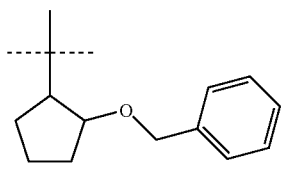 | H | 480.2 | ** |
| 91. | H | — | 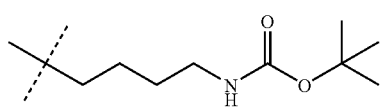 | H | 477.1 | *** |
| 92. | H | — | 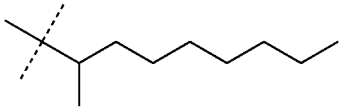 | H | 432.4 | * |

TABLE-continued
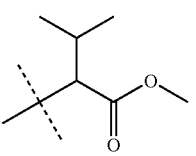
| Example No. | X | W | R | R' | MS MH+ | Activity |
|---|---|---|---|---|---|---|
| 93. | H | — | 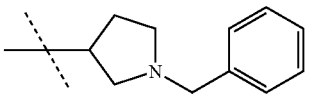 | H | 420.1 | ** |
| 94. | H | — | 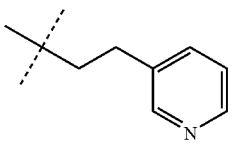 | H | 465.3 | *** |
| 95. | H | — | 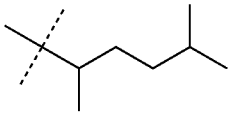 | H | 411.4 | *** |
| 96. | H | — | 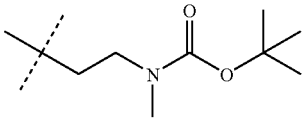 | H | 404.3 | ** |
| 97. | H | — | 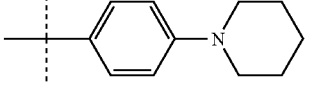 | H | 463.0 | ** |
| 98. | H | — | 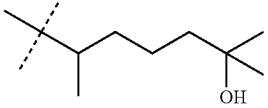 | H | 465.4 | ** |
| 99. | H | — | 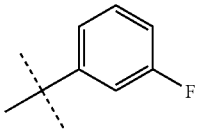 | H | 434.4 | ** |
| 100. | H | — |  | H | 400.3 | * |

TABLE-continued
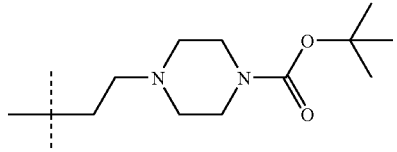
| Example No. | X | W | R | R' | MS MH+ | Activity |
|---|---|---|---|---|---|---|
| 101. | H | — | 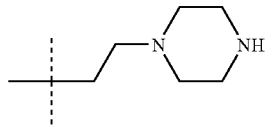 | H | 518.4 | *** |
| 102. | H | — | 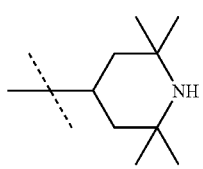 | H | 418.4 | ** |
| 103. | H | — | 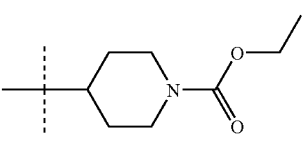 | H | 445.4 | *** |
| 104. | H | — | 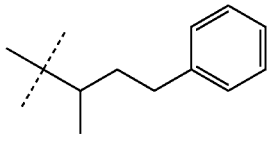 | H | 461.4 | ** |
| 105. | H | — | 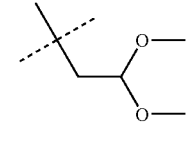 | H | 438.4 | * |
| 106. | H | — | 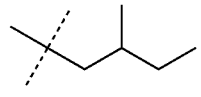 | H | 394.3 | ** |
| 107. | H | — | 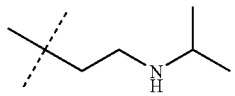 | H | 376.3 | ** |
| 108. | H | — |  | H | 391.4 | *** |

TABLE-continued
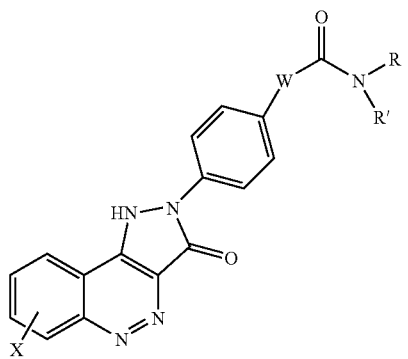
| Example No. | X | W | R | R' | MS MH+ | Activity |
|---|---|---|---|---|---|---|
| 109. | H | — | 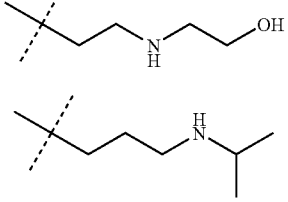 | H | 393.4 | *** |
| 110. | H | — | 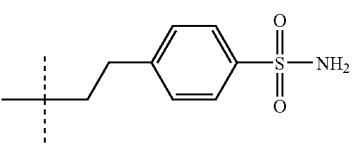 | H | 405.5 | *** |
| 111. | H | — | CH₂CH₂CH₂OH | H | 364.4 | ** |
| 112. | H | — | CH₂CH₂CH₂CH₂OH | H | 392.4 | *** |
| 113. | H | — | nHexyl | H | 390.4 | ** |
| 114. | H | — | 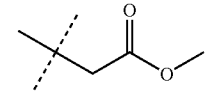 | H | 489.4 | ** |
| 115. | H | — | 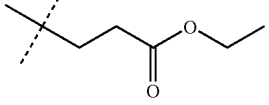 | H | 378.4 | ** |
| 116. | H | — | 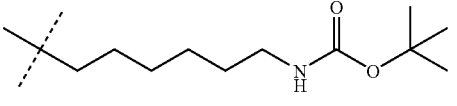 | H | 406.4 | * |
| 117. | H | — | 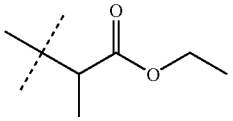 | H | 505.5 | ** |
| 118. | H | — | 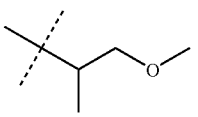 | H | 406.4 | ** |
| 119. | H | — | 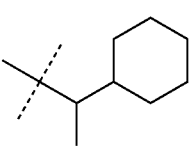 | H | 378.4 | ** |
| 120. | H | — |  | H | 416.4 | ** |

TABLE-continued

| Example No. | X | W | R | R' | MS MH+ | Activity |
|---|---|---|---|---|---|---|
| 121. | H | — | (pinane-type structure) | H | 442.4 | ** |
| 122. | H | — | (pinane-type structure) | H | 442.4 | * |
| 123. | H | NH | 4-benzylpiperidinyl (gem-dimethyl) | H | 494.3 | ** |
| 124. | H | NH | branched alkyl | H | 405.3 | * |
| 125. | H | NH | piperidinyl-propyl (gem-dimethyl) | H | 432.3 | ** |
| 126. | H | NH | 4-fluorobenzyl (gem-dimethyl) | H | 429.3 | * |
| 127. | H | NH | cyclohexyl (gem-dimethyl) | H | 403.3 | * |
| 128. | H | NH | CH$_2$CH$_2$CH$_2$OEt | H | 407.2 | ** |
| 129. | H | NH | 4-methylpiperazinyl-propyl (gem-dimethyl) | H | 461.3 | *** |
| 130. | H | NH | CH$_2$CH$_2$NMe$_2$ | H | 392.2 | *** |
| 131. | H | NH | allyl | H | 361.3 | *** |

TABLE-continued

| Example No. | X | W | R | R' | MS MH+ | Activity |
|---|---|---|---|---|---|---|
| 132. | H | NH | (CH₂ group linked to N-morpholine via neopentyl) | H | 434.3 | *** |
| 133. | H | NH | CH₂CH₂CH₂OMe | H | 393.2 | ** |
| 134. | H | NH | (neopentyl-CH₂CH₂-NH-cyclohexyl) | H | 460.3 | *** |
| 135. | H | NH | (neopentyl-2,2,6,6-tetramethyl-1-methylpiperidin-4-yl) | H | 474.3 | ** |
| 136. | H | NH | (CH₂)₃C(O)OEt neopentyl linker | H | 420.1 | * |
| 137. | H | NH | (branched alkyl with terminal C(CH₃)₂OH) | H | 449.2 | ** |
| 138. | H | NH | (neopentyl-iPr) | H | 377.3 | ** |
| 139. | H | NH | iPr | H | 363.3 | ** |
| 140. | H | NH | CH₂CH₂OMe | H | 379.3 | ** |
| 141. | H | NH | CH₂CH₂NHiPr | H | 406.2 | *** |
| 142. | H | NH | CH₂CH₂NHMe | H | 378.2 | *** |
| 143. | H | NH | CH₂CH₂NHEt | H | 392.2 | *** |
| 144. | H | NH | CH₂CH₂NHnPr | H | 406.2 | *** |
| 145. | H | NH | CH₂CH₂OCH₂CH₂OH | H | 409.2 | *** |
| 146. | H | NH | CH₂CH₂OH | H | 365.2 | *** |
| 147. | H | NH | CH₂CH₂Ph | H | 425.3 | ** |
| 148. | H | NH | CH₂CH₂CH₂NHiPr | H | 420.2 | *** |
| 149. | H | NH | CH₂CH₂CH₂OiPr | H | 421.2 | ** |
| 150. | H | NH | CH₂CH₂CH₂OH | H | 379.2 | *** |
| 151. | H | NH | CH₂CH₂CH₂CH₂CH₂OH | H | 407.2 | ** |

TABLE-continued

| Example No. | X | W | R | R' | MS MH+ | Activity |
|---|---|---|---|---|---|---|
| 152. | H | NH | (1-naphthylamino)propyl with gem-dimethyl | H | 490.1 | * |
| 153. | H | NH | (2-oxotetrahydrofuran-3-yl)methyl with gem-dimethyl | H | 405.3 | ** |
| 154. | H | NH | methyl ester with gem-dimethyl | H | 393.1 | ** |
| 155. | H | NH | 4-nitrophenethyl with gem-dimethyl | H | 470.3 | ** |
| 156. | H | NH | ethyl butanoate with gem-dimethyl | H | 421.2 | ** |
| 157. | H | NH | propanamide with gem-dimethyl | H | 378.1 | ** |
| 158. | H | NH | ethyl 2-methylpropanoate with gem-dimethyl | H | 421.1 | ** |
| 159. | H | NH | $CH_2CH_2CH_2OC_{12}H_{25}$ | H | 547.3 | *** |
| 160. | H | NH | $CH_2CH_2CH_2OnBu$ | H | 435.2 | * |
| 161. | H | NH | $CH_2CH_2CH_2SMe$ | H | 409.2 | ** |
| 162. | H | NH | (1-ethylpyrrolidin-2-yl)methyl with gem-dimethyl | H | 432.3 | *** |

TABLE-continued
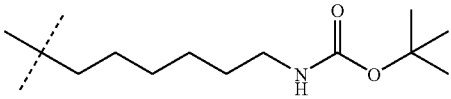
| Example No. | X | W | R | R' | MS MH+ | Activity |
|---|---|---|---|---|---|---|
| 163. | H | NH | 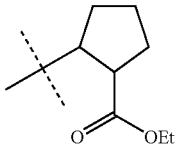 | H | 519.9 | ** |
| 164. | H | NH | 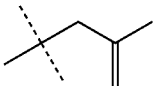 | H | 461.2 | * |
| 165. | H | NH | 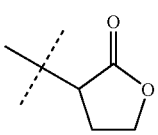 | H | 375.2 | ** |
| 166. | H | NH | 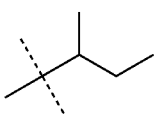 | H | 405.2 | ** |
| 167. | H | NH | 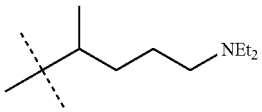 | H | 377.3 | ** |
| 168. | H | NH | 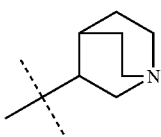 | H | 462.4 | *** |
| 169. | H | NH | 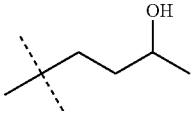 | H | 430.3 | *** |
| 170. | H | NH | CH$_2$CH$_2$CHO | H | 377.2 | * |
| 171. | H | NH |  | H | 393.3 | *** |

TABLE-continued
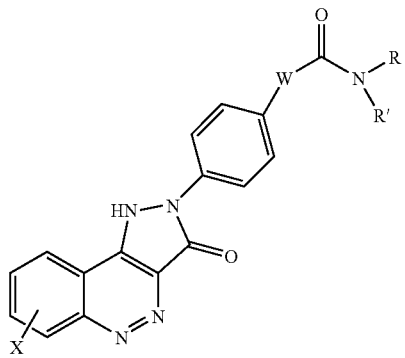
| Example No. | X | W | R | R' | MS MH+ | Activity |
|---|---|---|---|---|---|---|
| 172. | H | NH | 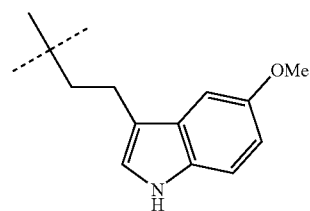 | H | 494.3 | ** |
| 173. | H | NH | 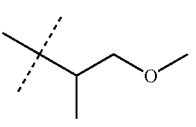 | H | 391.3 | ** |
| 174. | H | NH | 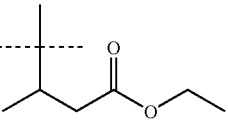 | H | 393.2 | ** |
| 175. | H | NH | 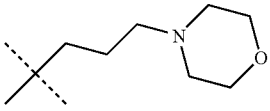 | H | 435.2 | ** |
| 176. | H | — | $CH_2CH_2CH_2NEt_2$ | H | 419.4 | *** |
| 177. | H | NH | nBu | H | 377.4 | ** |
| 178. | H | NH | $CH_2CH_2SMe$ | H | 395.3 | ** |
| 179. | H | NH | 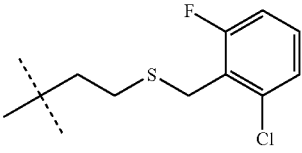 | H | 448.4 | *** |
| 180. | H | NH | 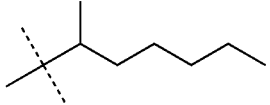 | H | 523.3 | * |
| 181. | H | NH |  | H | 419.4 | * |

TABLE-continued

| Example No. | X | W | R | R' | MS MH+ | Activity |
|---|---|---|---|---|---|---|
| 182. | H | NH | CH₂C(CH₃)₂CH₂NHC(O)OC(CH₃)₃ | H | 464.3 | ** |
| 183. | H | NH | CH₂-(1-methylpiperidin-4-yl) | H | 418.4 | *** |
| 184. | H | NH | CH₂CH₂-(pyridin-4-yl) | H | 426.3 | ** |
| 185. | H | NH | CH₂C(CH₃)₂CH₂N(CH₃)₂ | H | 434.4 | *** |
| 186. | H | NH | (CH₂)₃-(2-methylpiperidin-1-yl) | H | 460.4 | *** |
| 187. | H | NH | CH(Et)₂ | H | 391.4 | ** |
| 188. | H | NH | CH₂CH₂CH₂CH₂Ph | H | 453.4 | * |
| 189. | H | NH | CH(CO₂Et)CH₂CH₂CO₂Et | H | 507.5 | ** |
| 190. | H | NH | 4-hydroxycyclohexyl | H | 419.4 | ** |
| 191. | H | NH | CH₂CH₂N⁺(CH₃)₃ | H | 406.4 | ?? |
| 192. | H | NH | (CH₂)₃CO₂Et | H | 435.4 | * |

TABLE-continued
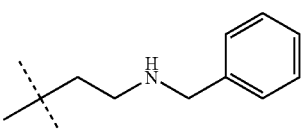
| Example No. | X | W | R | R' | MS MH+ | Activity |
|---|---|---|---|---|---|---|
| 193. | H | NH | 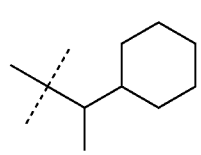 | H | 454.5 | *** |
| 194. | H | NH | 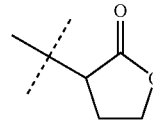 | H | 431.5 | * |
| 195. | H | NH | 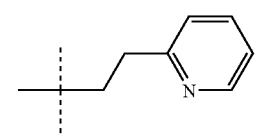 | H | 405.4 | ** |
| 196. | H | NH | 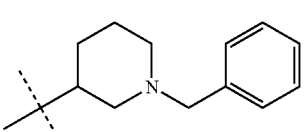 | H | 426.4 | ** |
| 197. | H | NH | 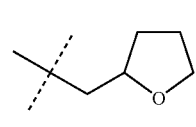 | H | 494.5 | ** |
| 198. | H | NH | 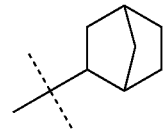 | H | 405.4 | ** |
| 199. | H | NH | 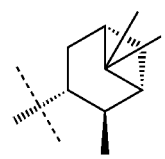 | H | 415.5 | * |
| 200. | H | NH | CH$_2$CH$_2$SCH$_2$Ph | H | 471.4 | * |
| 201. | H | NH | | H | 457.5 | * |

TABLE-continued

| Example No. | X | W | R | R' | MS MH+ | Activity |
|---|---|---|---|---|---|---|
| 202. | H | NH | (bornyl group) | H | 457.4 | * |
| 203. | H | NH | (1,1-dimethylbutyl group) | H | 391.4 | * |
| 204. | H | NH | CH$_2$cycloheptyl | H | 431.5 | * |
| 205. | H | NH | (tert-butyl ester group) | H | 435.4 | * |
| 206. | H | NH | CH$_2$CH$_2$N(nBu)$_2$ | H | 476.5 | *** |
| 207. | H | NH | (2-methylhexyl group) | H | 405.4 | ** |
| 208. | H | NH | CH$_2$CH$_2$OPh | H | 441.4 | ** |
| 209. | H | NH | (methacrylate ester group) | H | 433.4 | * |
| 210. | H | NH | (methoxymethyl isobutyl group) | H | 393.4 | *** |
| 211. | H | NH | (2-benzyloxycyclopentyl group) | H | 495.5 | * |
| 212. | H | NH | (2-benzyloxycyclohexyl group) | H | 509.4 | * |

TABLE-continued
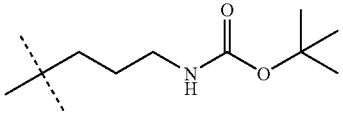
| Example No. | X | W | R | R' | MS MH+ | Activity |
|---|---|---|---|---|---|---|
| 213. | H | NH | 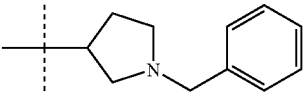 | H | 478.5 | ** |
| 214. | H | NH | 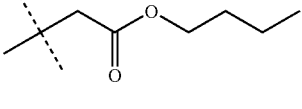 | H | 480.4 | *** |
| 215. | H | NH | 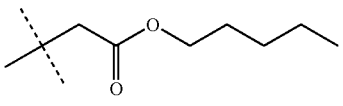 | H | 435.4 | * |
| 216. | H | NH | 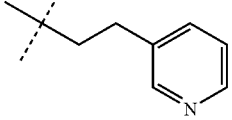 | H | 449.4 | * |
| 217. | H | NH | 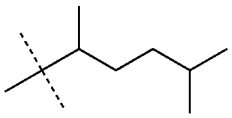 | H | 426.4 | ** |
| 218. | H | NH | 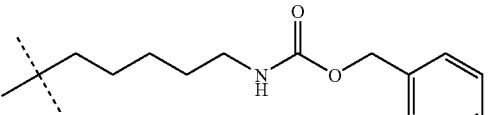 | H | 419.5 | * |
| 219. | H | NH | 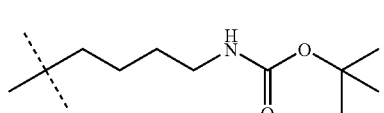 | H | 540.5 | ** |
| 220. | H | NH | 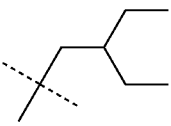 | H | 492.5 | * |
| 221. | H | NH | | H | 405.5 | * |

TABLE-continued
| Example No. | X | W | R | R' | MS MH+ | Activity |
|---|---|---|---|---|---|---|
| 222. | H | NH | 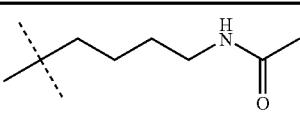 | H | 434.4 | *** |
| 223. | H | NH | 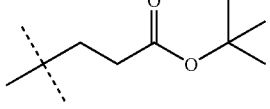 | H | 449.4 | ** |
| 224. | H | NH | 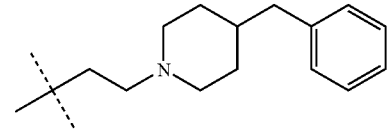 | H | 522.5 | *** |
| 225. | H | NH | 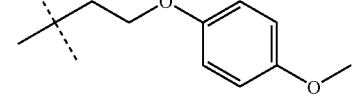 | H | 471.4 | * |
| 226. | H | NH | 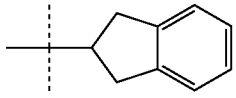 | H | 437.4 | * |
| 227. | H | NH | 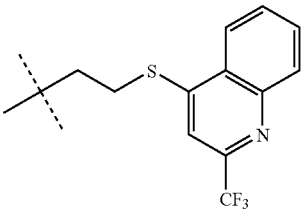 | H | 576.4 | * |
| 228. | H | NH | 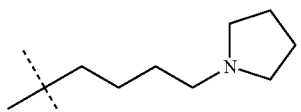 | H | 446.4 | *** |
| 229. | H | NH | 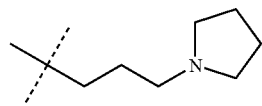 | H | 432.4 | *** |
| 230. | H | NH | 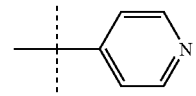 | H | 383.3 | * |

TABLE-continued
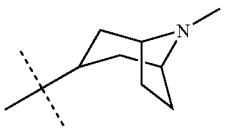
| Example No. | X | W | R | R' | MS MH+ | Activity |
|---|---|---|---|---|---|---|
| 231. | H | NH | 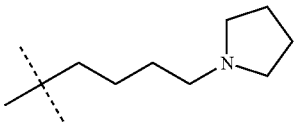 | H | 429.4 | *** |
| 232. | 6-F | — | CH₂CH₂CH₂NMe₂ | H | 409.4 | *** |
| 233. | 6-F | — | 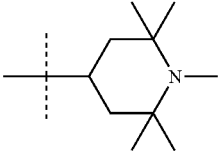 | H | 449.4 | *** |
| 234. | 6-F | — | 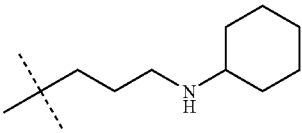 | H | 477.4 | *** |
| 235. | 6-F | — | 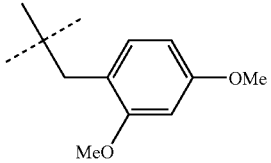 | H | 463.4 | *** |
| 236. | H | — | 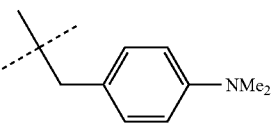 | H | 456.4 | * |
| 237. | H | — | 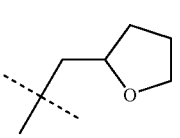 | H | 439.4 | *** |
| 238. | H | — |  | H | 390.3 | ** |
| 239. | H | — | cycloButyl | H | 360.4 | ** |

TABLE-continued

| Example No. | X | W | R | R' | MS MH+ | Activity |
|---|---|---|---|---|---|---|
| 240. | H | — | 4-MeO-benzyl (neopentyl-linked) | H | 426.4 | *** |
| 241. | H | — | nButyl | H | 362.4 | ** |
| 242. | H | — | 2-furyl-methyl (neopentyl-linked) | H | 386.4 | *** |
| 243. | H | — | iPr | H | 348.4 | *** |
| 244. | H | — | cyclohexyl-methyl (neopentyl-linked) | H | 402.4 | ** |
| 245. | H | — | nHeptyl | H | 404.4 | ** |
| 246. | H | — | Allyl | H | 346.3 | *** |
| 247. | H | — | $CH_2CH_2CH_2OMe$ | H | 378.4 | *** |
| 248. | H | — | 3-CF₃-benzyl (neopentyl-linked) | H | 464.3 | * |
| 249. | H | — | 2-CF₃-benzyl (neopentyl-linked) | H | 464.3 | * |
| 250. | H | — | 3-F-benzyl (neopentyl-linked) | H | 414.3 | *** |
| 251. | H | — | nPentyl | H | 376.4 | * |

TABLE-continued

| Example No. | X | W | R | R' | MS MH+ | Activity |
|---|---|---|---|---|---|---|
| 252. | H | — | indanyl | H | 422.3 | * |
| 253. | H | — | (3,5-dimethylphenyl)methyl | H | 442.3 | * |
| 254. | H | — | CH2CH2S-CH2-(2-chloro-6-fluorophenyl) | H | 508.2 | * |
| 255. | H | — | CH2CH2-(2-thienyl) | H | 416.3 | * |
| 256. | H | — | (piperidin-4-yl)methyl | H | 403.4 | ** |
| 257. | H | — | (2,4-dimethoxyphenyl)methyl | H | 456.4 | * |
| 258. | H | — | sec-pentyl | H | 362.3 | ** |
| 259. | H | — | CH2CH2-pyrrolidin-1-yl | H |  | *** |

TABLE-continued
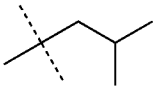
| Example No. | X | W | R | R' | MS MH+ | Activity |
|---|---|---|---|---|---|---|
| 260. | H | — | 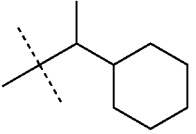 | H | | ** |
| 261. | H | NH | 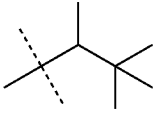 | H | 431.5 | * |
| 262. | H | NH | 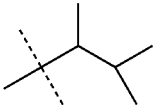 | H | 405.4 | * |
| 263. | H | NH | 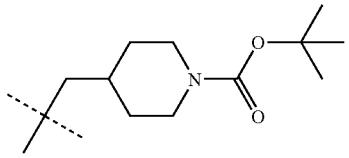 | H | 391.4 | ** |
| 264. | H | NH | 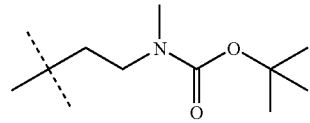 | H | 518.5 | * |
| 265. | H | NH | 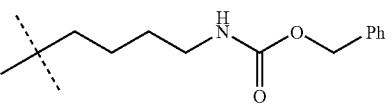 | H | | * |
| 266. | H | — | 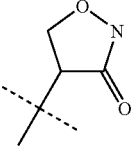 | H | 511.4 | *** |
| 267. | H | — |  | H | 391.4 | ** |

TABLE-continued

| Example No. | X | W | R | R' | MS MH+ | Activity |
|---|---|---|---|---|---|---|
| 268. | H | — | (3-(1H-indol-3-yl)propyl) | H | 449.4 | ** |
| 269. | H | — | CH₂CH₂NHnPr | H | 391.4 | * |
| 270. | H | — | CH₂CH₂Ph | H | 410.4 | * |
| 271. | H | — | CH₂CH₂CH₂CH₂CH₂NH₂ | H | 405.4 | *** |
| 272. | H | — | (3-(cyclohex-1-enyl)propyl) | H | 414.4 | * |
| 273. | H | — | CH₂CH₂CH₂OC₁₂H₂₅ | H | 532.6 | * |
| 274. | H | — | CH₂CH₂CH₂SCH₃ | H | 394.4 | *** |
| 275. | H | — | (ethyl 2-cyclopentanecarboxylate) | H | 446.4 | ** |
| 276. | H | — | CH(Et)CH₂OCH₂Ph | H | 468.4 | ** |
| 277. | H | — | (3-(tetrahydrofuran-2-on-3-yl)) | H | 390.3 | ** |
| 278. | H | — | (quinuclidin-3-yl) | H | 415.4 | *** |
| 279. | H | — | CH₂CH₂NHnBu | H | 405.4 | *** |
| 280. | H | — | CH₂CH₂NHCH₂CH₂NEt₂ | H | 448.5 | *** |
| 281. | H | — | CH₂CH₂NHCH₂Ph | H | 439.4 | *** |
| 282. | H | NH | Et | H | 349.4 | *** |
| 283. | H | NH | (farnesyl) | H | 457.4 | * |

TABLE-continued
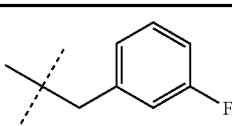
| Example No. | X | W | R | R' | MS MH+ | Activity |
|---|---|---|---|---|---|---|
| 284. | H | NH | 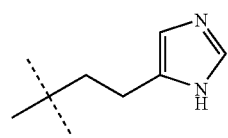 | H | 429.3 | * |
| 285. | H | NH | 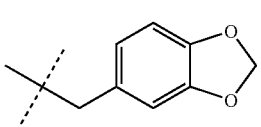 | H | 415.3 | *** |
| 286. | H | NH | 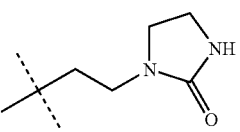 | H | 455.3 | * |
| 287. | H | NH | 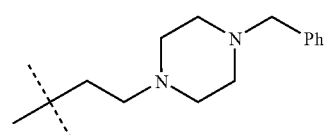 | H | 433.4 | *** |
| 288. | H | NH | 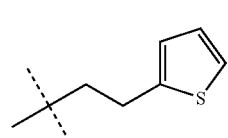 | H | 522.5 | *** |
| 289. | H | NH | 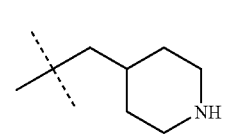 | H | 431.3 | ** |
| 290. | H | NH | 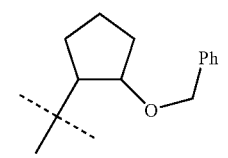 | H | 418.4 | *** |
| 291. | H | NH | CH$_2$CH$_2$CH$_2$Ph | H | 439.4 | * |
| 292. | H | NH |  | H | 495.4 | * |

TABLE-continued
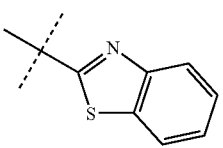
| Example No. | X | W | R | R' | MS MH+ | Activity |
|---|---|---|---|---|---|---|
| 293. | H | NH | 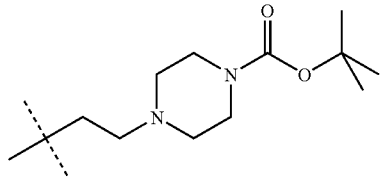 | H | 454.3 | * |
| 294. | H | NH | 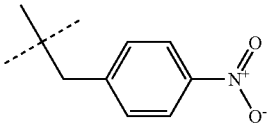 | H | 533.5 | ** |
| 295. | H | NH | CH$_2$CH$_2$NHCH$_3$ | H | 392.4 | *** |
| 296. | H | NH | 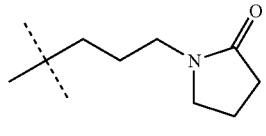 | H | 456.4 | * |
| 297. | H | NH | 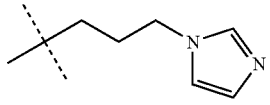 | H | 446.4 | ** |
| 298. | H | NH | 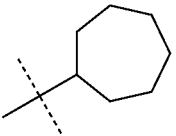 | H | 429.4 | *** |
| 299. | H | NH | 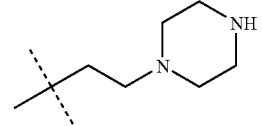 | H | 417.5 | * |
| 300. | H | NH |  | H | 433.5 | *** |

TABLE-continued

| Example No. | X | W | R | R' | MS MH+ | Activity |
|---|---|---|---|---|---|---|
| 301. | H | NH | 2,2,6,6-tetramethylpiperidin-4-yl | H | 460.5 | *** |
| 302. | H | NH | -CH₂C(CH₃)₂CH₂NH-(5-nitropyridin-2-yl) | H | 486.4 | * |
| 303. | H | NH | 1-(ethoxycarbonyl)piperidin-4-yl | H | 476.4 | * |
| 304. | H | NH | CH(CH₃)CH₂CH₂Ph | H | 453.4 | * |
| 305. | H | NH | 2,6-dimethylheptan-3-yl | H | 433.5 | * |
| 306. | H | NH | CH₂CH(OMe)₂ | H | 409.4 | *** |
| 307. | H | NH | CH₂CH(OEt)₂ | H | 437.5 | ** |
| 308. | H | NH | CH₂CH(CH₃)CH₂CH₃ | H | 391.4 | ** |
| 309. | H | NH | CH(CH₃)CH₂CH₃ | H | 377.4 | ** |
| 310. | H | NH | (1-ethylpyrrolidin-2-yl)methyl | H | 432.4 | *** |
| 311. | H | — | CH₂CHF₂ | H | 370.4 | *** |
| 312. | H | — | CH₂CH₂CF₃ | H | 402.4 | *** |
| 313. | H | — | adamantan-2-yl | H | 440.5 | ** |

TABLE-continued
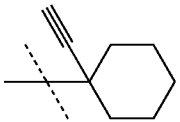
| Example No. | X | W | R | R' | MS MH+ | Activity |
|---|---|---|---|---|---|---|
| 314. | H | — | 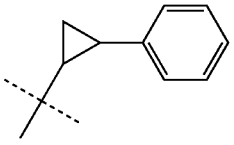 | H | 412.5 | *** |
| 315. | H | — | 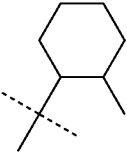 | H | 422.5 | ** |
| 316. | H | — | 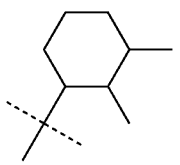 | H | 402.5 | ** |
| 317. | H | — |  | H | 416.5 | ** |
| 318. | H | — | 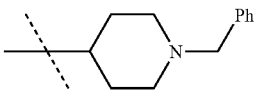 | H | 442.5 | *** |
| 319. | H | — | tBu | H | 362.5 | *** |
| 320. | H | — | $CH_2Si(CH_3)_3$ | H | 392.5 | * |
| 321. | H | — | $CH(CH_3)CH_2CH_3$ | H | 376.5 | *** |
| 322. | H | — | $CH(CH_3)CH_2CH_2CH_3$ | H | 390.5 | *** |
| 323. | 6-F | — | 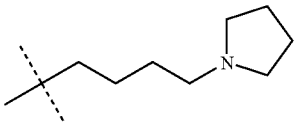 | H | 497.6 | *** |
| 324. | 6-F | NH | $CH_2CH_2N(CH_3)_2$ | H | 410.5 | *** |
| 325. | 8-F | — |  | H | 449.3 | *** |

TABLE-continued

| Example No. | X | W | R | R' | MS MH+ | Activity |
|---|---|---|---|---|---|---|
| 326. | 8-F | — | CH₂CH₂N(Et)₂ | H | 423.3 | *** |
| 327. | 8-F | — | | H | 435.3 | *** |
| 328. | 8-F | — | | H | 497.3 | *** |
| 329. | 8-F | — | CH₂CH₂CH₂N(Bu)₂ | H | 493.4 | *** |
| 330. | 8-F | — | CH₂CH₂CH₂N(Et)₂ | H | 437.3 | *** |
| 331. | 8-F | — | propyl) | H | 435.5 | *** |
| 332. | 8-F | — | propyl) | H | 463.3 | *** |
| 333. | 6-F | — | CH₂CH=CHCH₃ | H | 378.2 | *** |
| 334. | 6-F | — | piperidin-4-yl) | H | 525.3 | *** |
| 335. | 6-F | — | piperidin-4-yl) | H | 479.3 | *** |
| 336. | 6-F | — | piperidin-4-yl) | H | 517.4 | *** |
| 337. | 6-F | — | piperidin-4-yl) | H | 511.3 | *** |
| 338. | H | — | | H | 447.3 | *** |

TABLE-continued
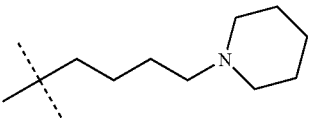
| Example No. | X | W | R | R' | MS MH+ | Activity |
|---|---|---|---|---|---|---|
| 339. | H | — | 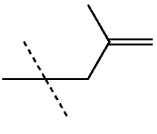 | H | 445.3 | *** |
| 340. | 6-F | — | 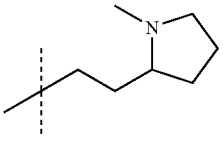 | H | 378.2 | *** |
| 341. | 6-F | — | CH₂CH₂NHnPr | H | 409.3 | *** |
| 342. | 6-F | — | CH₂CH₂N(Et)₂ | H | 423.3 | *** |
| 343. | 6-F | — | 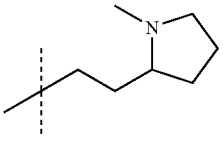 | H | 435.3 | *** |
| 344. | 6-F | — | CH₂CH₂NHnBu | H | 423.3 | *** |
| 345. | 6-F | — | CH₂CH₂CH₂N(nBu)₂ | H | 493.4 | *** |
| 346. | 6-F | — | CH₂CH₂CH₂N(Et)₂ | H | 437.3 | *** |
| 347. | 6-F | — | CH₂CH₂NHCH₂Ph | H | 457.3 | *** |
| 348. | 6-F | — | CH₂CH₂CH₂NHiPr | H | 423.3 | *** |
| 349. | 6-F | — | 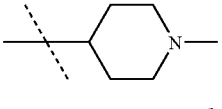 | H | 421.3 | *** |
| 350. | 6-F | — | 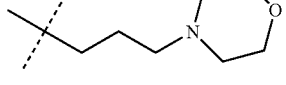 | H | 451.3 | *** |
| 351. | 6-F | — | CH₂CH₂CH₂NH₂ | H | 395.3 | *** |
| 352. | 6-F | — | 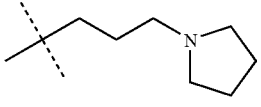 | H | 435.3 | *** |
| 353. | 6-F | — | 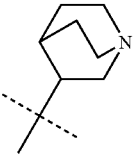 | H | 433.3 | *** |
| 354. | 6-F | — | CH₂CH₂CH₂OnBu | H | 438.3 | *** |
| 355. | 6-F | — | CH₂CH₂CH₂NHMe | H | 395.3 | *** |
| 356. | 6-F | — | CH₂CH₂NHMe | H | 381.3 | *** |

TABLE-continued
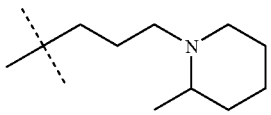
| Example No. | X | W | R | R' | MS MH+ | Activity |
|---|---|---|---|---|---|---|
| 357. | 6-F | — | CH₂CH₂NHEt | H | 395.3 | *** |
| 358. | 6-F | — | 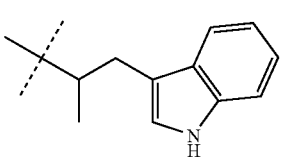 | H | 463.4 | *** |
| 359. | 6-F | — | 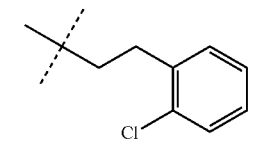 | H | 481.3 | *** |
| 360. | 6-F | — | 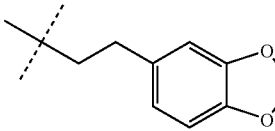 | H | 462.2 | ** |
| 361. | 6-F | — | 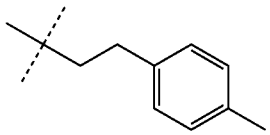 | H | 488.3 | *** |
| 362. | 6-F | — | 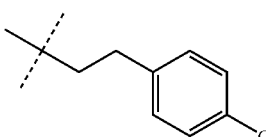 | H | 442.3 | ** |
| 363. | 6-F | — | 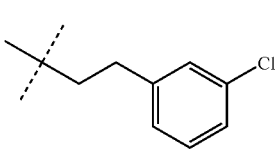 | H | 462.2 | ** |
| 364. | 6-F | — | 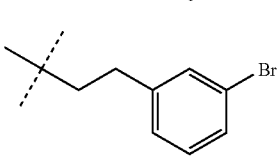 | H | 462.2 | ** |
| 365. | 6-F | — | | H | 506.2, 508.2 | * |

TABLE-continued
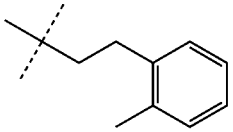
| Example No. | X | W | R | R' | MS MH+ | Activity |
|---|---|---|---|---|---|---|
| 366. | 6-F | — | 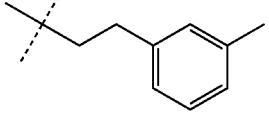 | H | 442.3 | ** |
| 367. | 6-F | — | 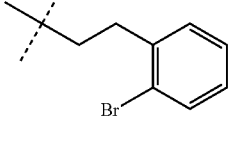 | H | 442.3 | ** |
| 368. | 6-F | — | 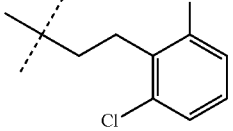 | H | 506.2, 508.2 | ** |
| 369. | 6-F | — | 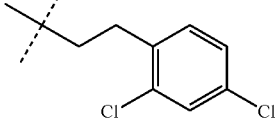 | H | 480.2 | ** |
| 370. | 6-F | — | 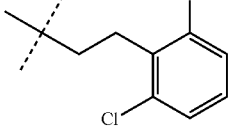 | H | 496.2 | ** |
| 371. | 6-F | — | 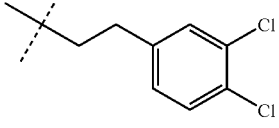 | H | 496.2 | ** |
| 372. | 6-F | — | 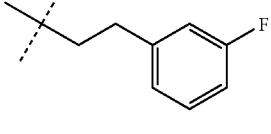 | H | 496.2 | ** |
| 373. | 6-F | — |  | H | 446.3 | ** |

TABLE-continued

| Example No. | X | W | R | R' | MS MH+ | Activity |
|---|---|---|---|---|---|---|
| 374. | 6-F | — | (2,2,6,6-tetramethylpiperidin-4-yl) | H | 463.3 | *** |
| 375. | 6-F | — | tBu | H | 380.3 | *** |
| 376. | 6-F | — | CH₂CHF₂ | H | 388.2 | *** |
| 377. | 6-F | — | CH₂CH=CH₂ | H | 364.2 | *** |
| 378. | 6-F | — | 4-(4-tBu-benzyl)piperidin-4-yl | H | 553.4 | *** |
| 379. | 6-F | — | 4-(3,5-dimethylbenzyl)piperidin-4-yl | H | 524.4 | ** |
| 380. | 6-F | — | 4-(4-SO₂Me-benzyl)piperidin-4-yl | H | 575.3 | *** |
| 381. | 8-F | — | CH₂CH₂CH₂N(Me)₂ | H | 409.3 | *** |
| 382. | 8-F | — | CMe₂CH₂CH₂NHCyclohexyl | H | 463.3 | *** |
| 383. | 8-F | — | CH₂CH₂NHEt | H | 409.3 | *** |
| 384. | 8-F | — | CH₂CH₂NHBu | H | 423.3 | *** |
| 385. | 8-F | — | CH₂CH₂CH₂NHiPr | H | 423.3 | *** |
| 386. | 8-F | — | CH₂CH₂CH₂CH₂OH | H | 396.3 | *** |
| 387. | 9-F | — | CH₂CH₂CH₂N(Me)₂ | H | 409.2 | *** |
| 388. | 9-F | — | CMe₂(CH₂)₃-pyrrolidin-1-yl | H | 449.2 | *** |

TABLE-continued

| Example No. | X | W | R | R' | MS MH+ | Activity |
|---|---|---|---|---|---|---|
| 389. | 9-F | — | *(CH₂)₃-NH-cyclohexyl)* | H | 463.3 | *** |
| 390. | 9-F | — | *(CH₂-(2,2,6,6-tetramethyl-1-methylpiperidin-4-yl))* | H | 477.3 | *** |
| 391. | 9-F | — | *(CH₂-(1-methylpiperidin-4-yl))* | H | 421.2 | *** |
| 392. | 9-F | — | CH₂CH₂CH₂N(Et)₂ | H | 437.2 | *** |
| 393. | 9-F | — | *(CH₂)₃-pyrrolidin-1-yl* | H | 435.2 | *** |
| 394. | 9-F | — | *(CH₂)₃-(2-methylpiperidin-1-yl)* | H | 463.2 | *** |
| 395. | 9-F | — | CH₂CH₂CH₂NHiPr | H | 423.2 | *** |
| 396. | 9-F | — | CH₂CH₂CH₂NHMe | H | 395.2 | *** |
| 397. | 9-F | — | *C(CH₃)₂-(CH₂)₃-morpholin-4-yl* | H | 451.2 | *** |
| 398. | 9-F | — | CH₂CH₂CH₂N(nBu)₂ | H | 493.3 | *** |
| 399. | 9-F | — | *(1-benzylpyrrolidin-3-yl)* | H | 483.2 | *** |
| 400. | 9-F | — | tBu | H | 380.2 | *** |

TABLE-continued
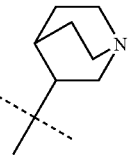
| Example No. | X | W | R | R' | MS MH+ | Activity |
|---|---|---|---|---|---|---|
| 401. | 9-F | — | 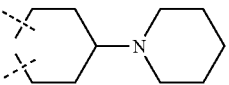 | H | 433.2 | *** |
| 402. | 9-F | — | 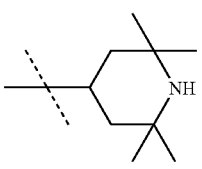 | | 475.2 | ** |
| 403. | 9-F | — | 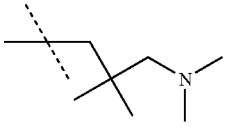 | H | 463.3 | *** |
| 404. | 9-F | — | 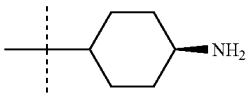 | H | 437.2 | *** |
| 405. | 9-F | — | 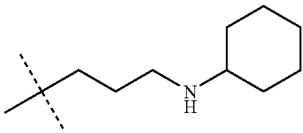 | H | 421.2 | *** |
| 406. | 8-Me | — | $CH_2CH_2CH_2N(Me)_2$ | H | 405.3 | *** |
| 407. | 8-Me | — | 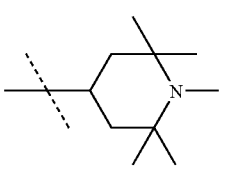 | H | 459.3 | *** |
| 408. | 8-Me | — | 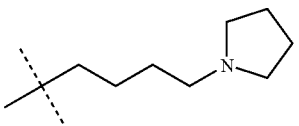 | H | 473.4 | *** |
| 409. | 8-Me | — |  | H | 445.3 | *** |

TABLE-continued
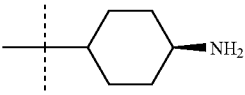
| Example No. | X | W | R | R' | MS MH+ | Activity |
|---|---|---|---|---|---|---|
| 410. | 6-F | — | 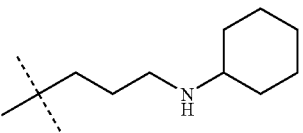 | H | 421.3 | *** |
| 411. | 6-Cl | — | CH₂CH₂CH₂N(Me)₂ | H | 425.3 | *** |
| 412. | 6-Cl | — | 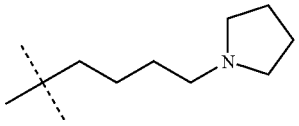 | H | 479.2 | *** |
| 413. | 6-Cl | — | 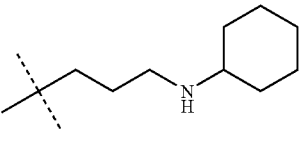 | H | 465.3 | *** |
| 414. | 6,8-diF | — | CH₂CH₂CH₂N(Me)₂ | H | 427.3 | *** |
| 415. | 6,8-diF | — | 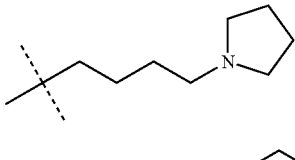 | H | 481.3 | *** |
| 416. | 6,8-diF | — | 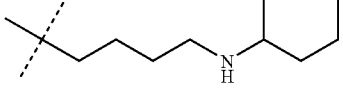 | H | 467.2 | *** |
| 417. | 6-F | — | 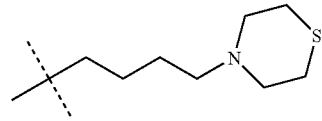 | H |  | *** |
| 418. | 8-MeO | — | CH₂CH₂CH₂NHMe | H | 407.2 | *** |
| 419. | 6-F | — | 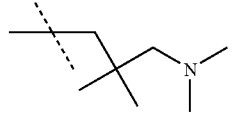 | H | 481.2 | *** |
| 420. | 6-F | — |  | H | 437.2 | *** |

TABLE-continued

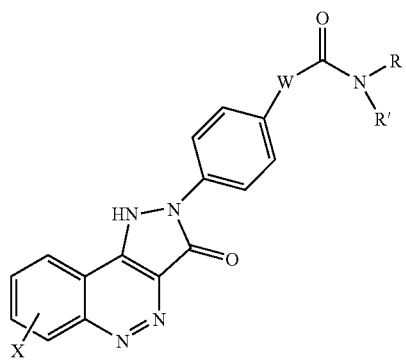

| Example No. | X | W | R | R' | MS MH+ | Activity |
|---|---|---|---|---|---|---|
| 421. | 6-F | — | ![piperidinyl-cyclohexyl] | | 475.2 | ** |
| 422. | 6-F | — | CH₂CF₂CF₂CF₃ | H | 456.1 | *** |
| 423. | 6-F | — | CH₂CH₂CF₃ | H | 420.1 | *** |
| 424. | 6-F | — | ![cyclobutyl-dimethyl] | H | 378.1 | *** |
| 425. | 6-F | — | ![cyclopentyl-dimethyl] | H | 392.2 | *** |
| 426. | 6-F | — | CH₂CH₂F | H | 370.1 | *** |
| 427. | 8-F | — | ![tetramethylpiperidinyl] | H | 477.3 | *** |
| 428. | 6,9-diF | — | CH₂CH₂CH₂NHMe | H | 413.2 | *** |
| 429. | 6,9-diF | — | ![cyclohexylaminopropyl] | H | 481.3 | *** |
| 430. | 6,9-diF | — | ![pyrrolidinyl-butyl] | H | 467.2 | *** |
| 431. | 6,9-diF | — | ![tetramethylpiperidinyl] | H | 495.3 | *** |
| 432. | 6-F | — | CH₂CH₂CH₂CH₂N(Et)Me | H | 437.2 | *** |
| 433. | 6-F | — | CH₂CH₂CH₂CH₂N(Et)₂ | H | 451.3 | *** |

TABLE-continued
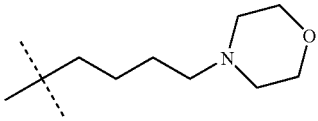
| Example No. | X | W | R | R' | MS MH+ | Activity |
|---|---|---|---|---|---|---|
| 434. | 6-F | — | 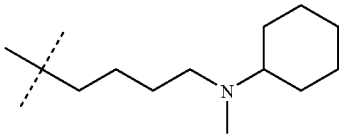 | H | 465.2 | *** |
| 435. | 6-F | — | CH₂CH₂CH₂CH₂N(Me)CH₂CH=CH₂ | H | 449.2 | *** |
| 436. | 6-F | — | 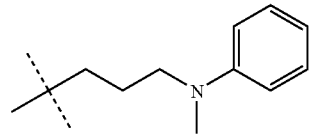 | H | 491.4 | *** |
| 437. | 6-F | — | CH₂CH₂CH₂CH₂F | H | 398.2 | *** |
| 438. | 6-F | — | 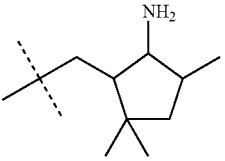 | H | 471.2 | ** |
| 439. | 6-F | — | 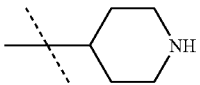 | H | 463.3 | *** |
| 440. | 6-F | — | 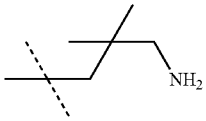 | H | 407.2 | *** |
| 441. | 6-F | — | 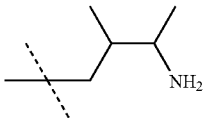 | H | 409.3 | *** |
| 442. | 6-F | — | CH₂CH₂CH₂NHnPr | H | 423.2 | *** |
| 443. | 6-F | — | 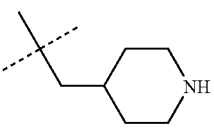 | H | 409.2 | *** |
| 444. | 6-F | — |  | H | 421.1 | *** |

TABLE-continued
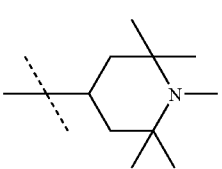
| Example No. | X | W | R | R' | MS MH+ | Activity |
|---|---|---|---|---|---|---|
| 445. | 6-F | — | CH₂CH₂CH₂NH₂ | H | 381.2 | *** |
| 446. | 8-Cl | — | CH₂CH₂CH₂N(Me)₂ | H | 425.2 | *** |
| 447. | 8-Cl | — | 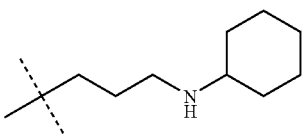 | H | 493.2 | *** |
| 448. | 8-Cl | — | 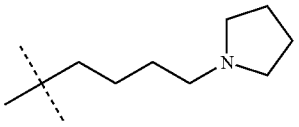 | H | 479.3 | *** |
| 449. | 8-Cl | — | 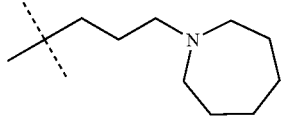 | H | 465.2 | *** |
| 450. | 6-F | — | Et | H | 352.2 | *** |
| 451. | 6-F | — | 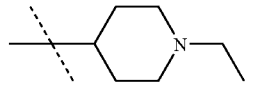 | H | 463.3 | *** |
| 452. | 6-F | — | Et | nPr | 394.2 | ** |
| 453. | 6-F | — | 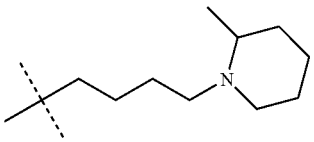 | H | 435.2 | *** |
| 454. | 6-F | — | 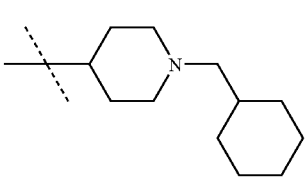 | H | 477.3 | *** |
| 455. | 6-F | — | CH₂tBu | H | 394.2 | *** |
| 456. | 6-F | — | 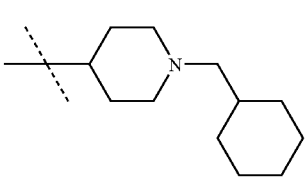 | H | 503.3 | *** |

TABLE-continued
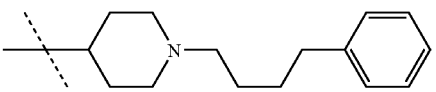
| Example No. | X | W | R | R' | MS MH+ | Activity |
|---|---|---|---|---|---|---|
| 457. | 6-F | — | 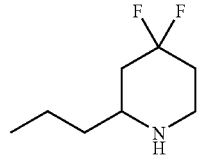 | H | 539.3 | *** |
| 458. | 6-F | — | 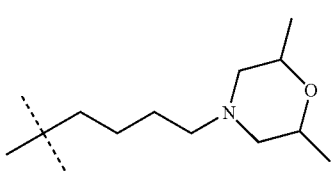 | H | 471.2 | *** |
| 459. | 6-F | — | CH$_2$CH$_2$CH$_2$CH$_2$N(CH$_2$CH=CH$_2$)$_2$ | H | 475.3 | *** |
| 460. | 6-F | — | 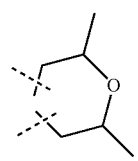 | H | 493.3 | *** |
| 461. | 6-F | — | 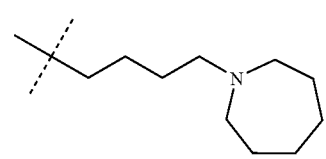 | | 422.2 | *** |
| 462. | 6-F | — | 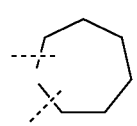 | H | 477.3 | *** |
| 463. | 6-F | — | 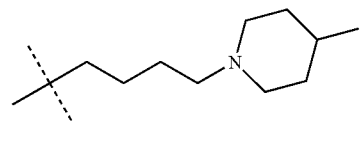 | | 406.2 | *** |
| 464. | 6-F | — |  | H | 477.3 | *** |
| 465. | 6-F | — |  | | 406.2 | *** |

TABLE-continued
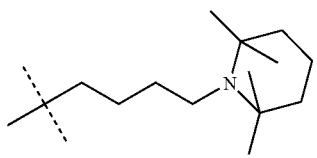
| Example No. | X | W | R | R' | MS MH+ | Activity |
|---|---|---|---|---|---|---|
| 466. | 6-F | — | 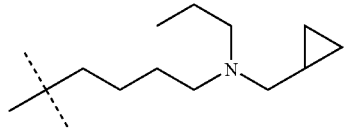 | H | 519.2 | *** |
| 467. | 6-F | — | $CH_2CF_2CF_2H$ | H | 438.1 | *** |
| 468. | 6-F | — | 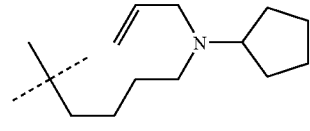 | H | 491.3 | *** |
| 469. | 6-F | — | 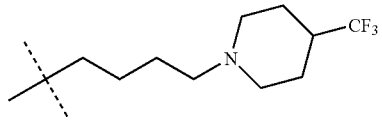 | H | 503.3 | *** |
| 470. | 6-F | — | 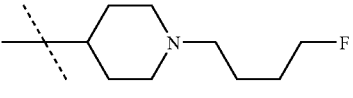 | H | 531.3 | *** |
| 471. | 6-F | — | 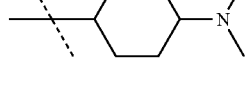 | H | 481.2 | *** |
| 472. | 6-F | — | 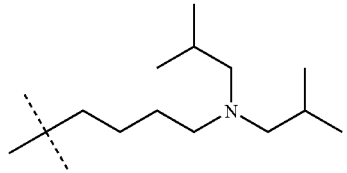 | H | 449.3 | *** |
| 473. | 8-F | — | $CH_2CF_2H$ | H | 388.1 | *** |
| 474. | 6-F | — | allyl | allyl | 404.2 | ** |
| 475. | 6-F | — | $CH_2CH_2CF=CF_2$ | H | 432.1 | ** |
| 476. | 6-F | — |  | H | 507.3 | *** |

TABLE-continued
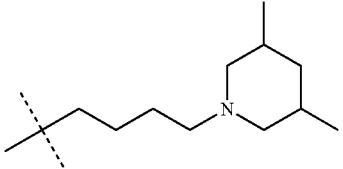
| Example No. | X | W | R | R' | MS MH+ | Activity |
|---|---|---|---|---|---|---|
| 477. | 6-F | — | 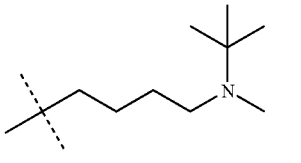 | H | 491.3 | *** |
| 478. | 6-F | — | 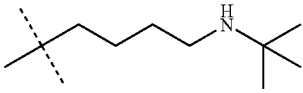 | H | 465.3 | *** |
| 479. | 6-F | — | 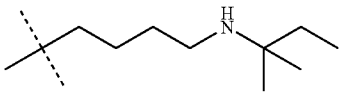 | H | 451.2 | *** |
| 480. | 6-F | — | 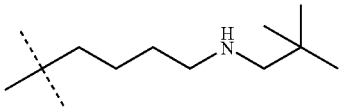 | H | 465.2 | *** |
| 481. | 6-F | — | 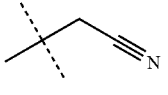 | H | 465.2 | *** |
| 482. | 6-F | — | 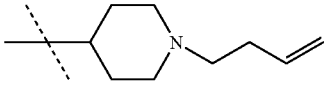 | H | 363.1 | *** |
| 483. | 6-F | — | 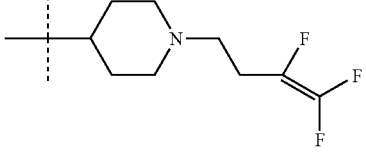 | H | 461.3 | *** |
| 484. | 6-F | — | 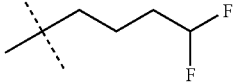 | H | 515.3 | *** |
| 485. | 6-F | — | | H | 416.2 | *** |

TABLE-continued

| Example No. | X | W | R | R' | MS MH+ | Activity |
|---|---|---|---|---|---|---|
| 486. | 6-F | — | (CH₂)₂C≡N with gem-dimethyl | H | 377.1 | *** |
| 487. | 6-F | — | C(CH₂OH)₃ | H | 428.2 | *** |
| 488. | 6-F | — | gem-dimethyl-pyrrolidine | H | 393.1 | *** |
| 489. | 6-F | — | N-methyl azepane | | 421.2 | *** |
| 490. | 6-F | — | azepane (NH) | | 407.1 | *** |
| 491. | 6-F | — | CH₂CONH₂ | H | 381.2 | *** |
| 492. | 6-F | — | 4-(difluoromethylene)cyclohexyl | H | 454.1 | *** |
| 493. | 6-F | — | CH₂CH(F)CH₃ with gem-dimethyl | H | 398.1 | *** |
| 494. | 6-F | — | azepane | | 420.2 | ** |
| 495. | 6-F | — | decahydronaphthalenyl | | 446.2 | |
| 496. | 6-F | — | decahydronaphthalenyl | | 446.2 | |

TABLE-continued

| Example No. | X | W | R | R' | MS MH+ | Activity |
|---|---|---|---|---|---|---|
| 497. | 6-F | — | (2-phenyl-2-cyano-1,1-dimethylethyl) | H | 439.1 | ** |
| 498. | 6-F | — | (1-isopropyl-1-cyano-2,2-dimethylpropyl) | H | 419.2 | *** |
| 499. | 6-F | — | (3-amino-cyclohexyl-1,1-dimethylmethyl) | H | 421.2 | *** |
| 500. | 6,9-diF | — | CH$_2$CHF$_2$ | H | 406.2 | *** |
| 501. | 6-F | — | (trans-4-hydroxycyclohexyl-1,1-dimethylmethyl) | H | 422.2 | *** |
| 502. | 6-F | — | (4-hydroxy-1,1-dimethylpentyl) | H | 396.2 | *** |
| 503. | 6-F | — | (2-hydroxycycloheptylmethyl-dimethyl) | H | 450.2 | ** |
| 504. | 6-F | — | (2-hydroxycyclohexylmethyl-dimethyl) | H | 436.2 | ** |
| 505. | 6-F | — | CH$_2$CH$_2$NHCH$_2$CH$_2$OH | H | 411.2 | *** |
| 506. | 6-F | — | (2-hydroxycyclooctylmethyl-dimethyl) | H | 464.2 | ** |

TABLE-continued

| Example No. | X | W | R | R' | MS MH+ | Activity |
|---|---|---|---|---|---|---|
| 507. | 6-F | — | CH(CH₂OH)₂ | H | 398.1 | *** |
| 508. | 6-F | — | CH(CH₃)CH₂OH | H | 382.1 | *** |
| 509. | 6-F | — | CH(CH₂CH₃)CH₂OH | H | 396.2 | *** |
| 510. | 6-F | — | (1-methyl-2-hydroxy-indanyl) | H | 456.2 | ** |
| 511. | 6-F | — | (hydroxymethyl-(4-hydroxybenzyl)-methyl) | H | 474.1 | ** |
| 512. | 6-F | — | (hydroxy-diphenyl-methyl substituent) | H | 520.2 | * |
| 513. | 6-F | — | (hydroxymethyl-hydroxyphenyl-methyl) | H | 474.1 | ** |
| 514. | 6-F | — | (hydroxymethyl-benzyl-methyl) | H | 458.2 | *** |
| 515. | 6-F | — | (hydroxymethyl-indolylmethyl) | H | 497.2 | ** |
| 516. | 6-F | — | C(CH₃)₂CH₂OH | H | 396.2 | * |
| 517. | 6-F | — | C CH₃(CH₂OH)₂ | H | 412.1 | *** |

Examples of the result of testing the above compounds in the assay for inhibition of production of interleukin-2 (IL-2) by human Jurkat T cells, described above, are as follows:

| Example No (see table) | Compound Concentration (μM) | Percentage Inhibition (relative to DMSO = 0%) |
|---|---|---|
| 478 | 10 | 56.0 |
| 376 | 10 | 56.7 |
| 353 | 10 | 77.4 |
| 429 | 10 | 58.8 |
| 349 | 10 | 79.5 |
| 68 | 10 | 71.7 |
| 235 | 10 | 59.3 |
| 288 | 30 | 72 |
| 162 | 30 | 54.4 |
| 350 | 10 | 74.2 |
| 381 | 10 | 48.5 |
| 442 | 10 | 58.9 |
| 482 | 10 | 39.2 |
| 472 | 10 | 58.4 |
| 453 | 10 | 55.7 |
| 53 | 30 | 63.8 |

The invention claimed is:

1. An orally administrable pharmaceutical or veterinary composition comprising a compound together with a pharmaceutically or veterinarily acceptable excipient or carrier, wherein the compound is a compound of formula (I) or a pharmaceutically or veterinarily acceptable salt or hydrate thereof:

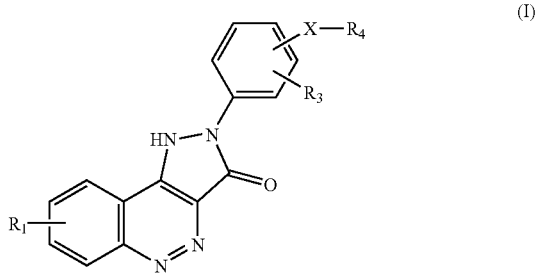

(I)

wherein
$R_1$ and $R_3$ independently represent H; F; Cl; Br; —$NO_2$; —CN; $C_1$-$C_6$ alkyl optionally substituted by F or Cl; or $C_1$-$C_6$ alkoxy optionally substituted by F;
$R_4$ represents a carboxylic acid group (—COOH) or an ester thereof, or —C(=O)$NR_6R_7$, —$NR_7$C(=O)$R_6$, —$NR_7$C(=O)$OR_6$, —NHC(=O)$NR_7R_6$ or —NHC(=S)$NR_7R_6$;
$R_6$ represents H, or a radical of formula -(Alk)$_m$-Q wherein m is 0 or 1, wherein Alk is an optionally substituted divalent straight or branched $C_1$-$C_{12}$ alkylene, or $C_2$-$C_{12}$ alkenylene, or $C_2$-$C_{12}$ alkynylene radical or a divalent $C_3$-$C_{12}$ carbocyclic radical, any of which radicals may contain one or more —O—, —S— or —N($R_8$)— links;
$R_8$ represents H or $C_1$-$C_4$ alkyl, $C_3$-$C_4$ alkenyl, $C_3$-$C_4$ alkynyl, or $C_3$-$C_6$ cycloalkyl;
Q represents H; —$NR_9R_{10}$ wherein $R_9$ and $R_{10}$ independently represent H; $C_1$-$C_4$ alkyl; $C_3$-$C_4$ alkenyl; $C_3$-$C_4$ alkynyl; $C_3$-$C_6$ cycloalkyl; an ester group; an optionally substituted carbocyclic or heterocyclic group; or $R_9$ and $R_{10}$ form a ring when taken together with the nitrogen to which they are attached, which ring is optionally substituted;
$R_7$ represents H or $C_1$-$C_6$ alkyl; or when taken together with the atom or atoms to which they are attached $R_6$ and $R_7$ form an optionally substituted monocyclic heterocyclic ring having 5, 6 or 7 ring atoms; and
X represents a bond or a divalent radical of formula —(Z)$_n$-(Alk)- or -(Alk)-(Z)$_n$—, wherein Z represents —O—, —S— or —NH— and Alk is as defined in relation to $R_6$ and n is 0 or 1.

2. The orally administrable composition of claim 1 wherein the radical $R_4$X— is in the 4-position of the phenyl ring.

3. The orally administrable composition of claim 1 wherein X is a bond.

4. The orally administrable composition of claim 1 wherein $R_3$ is hydrogen.

5. The orally administrable composition of claim 1 wherein $R_1$ is hydrogen or fluoro.

6. The orally administrable composition of claim 1 wherein $R_4$ represents —C(=O)$NR_6R_7$.

7. The orally administrable composition of claim 1 wherein $R_4$ represents —NHC(=O)$NR_7R_6$.

8. The orally administrable composition of claim 7 wherein $R_6$ is a quinuclidinyl radical.

9. The orally administrable composition of claim 1 wherein $R_6$ represents a radical of formula -(Alk)$_m$-Q wherein m is 1 and the divalent radical Alk contains 3 or 4 carbon atoms and is unsubstituted, and Q represents —$NR_9R_{10}$ wherein $R_9$ and $R_{10}$ independently represent H; $C_1$-$C_4$ alkyl; $C_3$-$C_4$ alkenyl; $C_3$-$C_4$ alkynyl; $C_3$-$C_6$ cycloalkyl; an ester group; an optionally substituted carbocyclic or heterocyclic group; or form a ring when taken together with the nitrogen to which they are attached, which ring is optionally substituted.

10. The orally administrable composition of claim 6 wherein $R_7$ is hydrogen.

11. The orally administrable composition of claim 1 wherein Q represents H; —$CF_3$; —OH; —SH; —$NR_8R_8$ wherein each $R_8$ independently represents H; $C_1$-$C_4$ alkyl; $C_3$-$C_4$ alkenyl; $C_3$-$C_4$ alkynyl; $C_3$-$C_6$ cycloalkyl; an ester group; an optionally substituted aryl, aryloxy, cycloalkyl, cycloalkenyl or heterocyclic group; or form a ring when taken together with the nitrogen to which they are attached; and $R_7$ represents H or $C_1$-$C_6$ alkyl; or when taken together with the atom or atoms to which they are attached $R_6$ and $R_7$ form a monocyclic heterocyclic ring having 5, 6 or 7 ring atoms.

12. The orally administrable composition of claim 11 wherein $R_4$ represents a carboxylic acid group (—COOH) or an ester group of formula —COOR wherein R is methyl, ethyl, n- or iso-propyl, n-, sec- or tert-butyl or benzyl.

13. The orally administrable composition of claim 12 wherein $R_6$ represents a radical of formula -(Alk)$_m$-Q wherein m is 1, Alk is —$CH_2$—, —$CH_2CH_2$—, —$CH_2CH_2CH_2$—, or —$CH_2CH(CH_3)CH_2$—, or a divalent cyclopropylene, cyclopentylene or cyclohexylene radical, optionally substituted by OH, oxo, $CF_3$, methoxy or ethoxy, and Q represents hydrogen; —$NR_8R_8$ wherein each $R_8$ may be the same or different and selected from hydrogen, methyl, ethyl, n- or isopropyl or tert-butyl; a methyl, ethyl or benzyl ester; or an optionally substituted phenyl, phenoxy, cyclopentyl, cyclohexyl, furyl, thienyl, piperidyl, or piperazinyl group.

14. The orally administrable composition of claim 11 wherein $R_7$ represents methyl, ethyl, n- or iso-propyl, n-, sec- or tert-butyl; or when taken together with the atom or atoms to which they are attached $R_6$ and $R_7$ form a monocyclic heterocyclic ring having 5, 6 or 7 ring atoms.

15. The orally administrable composition of claim 11 wherein $R_1$ is H, F, Cl, methyl, methoxy, or methylenedioxy.

16. The orally administrable composition of claim 11 wherein $R_1$ is F, in the 6-position of the 3-oxo-1,3-dihydro-2H-pyrazolo[4,3-c]cinnolin-2-yl ring system.

17. The orally administrable composition of claim 11 wherein $R_3$ is H, F, Cl, methyl, methoxy, or methylenedioxy.

18. The orally administrable composition of claim 11 wherein X is a bond, or a —$CH_2$— or —$CH_2CH_2$— radical.

19. The orally administrable composition of claim 1 wherein the compound is a compound of formula (IC) or a pharmaceutically or veterinarily acceptable salt or hydrate:

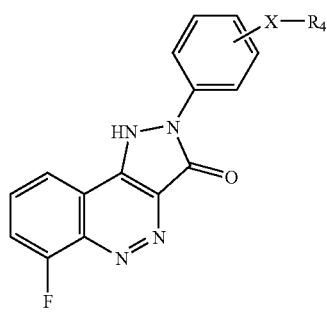

(IC)

wherein:
X is a bond, or a —$CH_2$— or —$CH_2CH_2$— radical and $R_4$ is a carboxylic acid group (—COOH), an ester group of formula —COOR wherein R is methyl, ethyl, n- or iso-propyl, n-, sec- or tert-butyl or benzyl, or —NHC(=O)$NR_6R_7$ wherein $R_6$ represents H, or a radical of formula -(Alk)$_m$-Q wherein m is 0 or 1;
Alk is an optionally substituted divalent straight or branched $C_1$-$C_{12}$ alkylene, or $C_2$-$C_{12}$ alkenylene, or $C_2$-$C_{12}$ alkynylene radical or a divalent $C_3$-$C_{12}$ carbocyclic radical, any of which radicals may contain one or more —O—, —S— or —N($R_8$)— links wherein $R_8$ represents H or $C_1$-$C_4$ alkyl, $C_3$-$C_4$ alkenyl, $C_3$-$C_4$ alkynyl, or $C_3$-$C_6$ cycloalkyl, and
Q represents H; —$NR_9R_{10}$ wherein $R_9$ and $R_{10}$ independently represents H; $C_1$-$C_4$ alkyl; $C_3$-$C_4$ alkenyl; $C_3$-$C_4$ alkynyl; $C_3$-$C_6$ cycloalkyl; an ester group; an optionally substituted carbocyclic or heterocyclic group; or $R_9$ and $R_{10}$ form a ring when taken together with the nitrogen to which they are attached, which ring is optionally substituted; and $R_7$ represents H or $C_1$-$C_6$ alkyl; or when taken together with the atom or atoms to which they are attached $R_6$ and $R_7$ form an optionally substituted monocyclic heterocyclic ring having 5, 6 or 7 ring atoms.

20. The orally administrable composition of claim 19 wherein the radical $R_4X$— is in the 4-position of the phenyl ring.

21. The orally administrable composition of claim 20 wherein X is a bond and $R_4$ is —C(=O)$NR_6R_7$.

22. The orally administrable composition of claim 1 wherein the compound is 4-(6-fluoro-3-oxo-1,3-dihydro-pyrazolo[4,3-c]cinnolin-2-yl)-N-(2,2-difluoro-ethylyl)-benzamide, of formula (A)

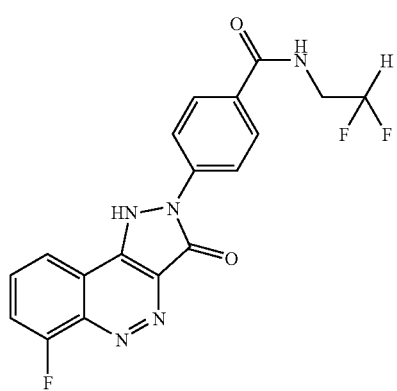

(A)

or a pharmaceutically or veterinarily acceptable salt or hydrate.

23. The orally administrable composition of claim 1 wherein the compound is N-[3-(tert-butyl-methyl-amino)-butyl]-4-(6-fluoro-3-oxo-1,3-dihydro-pyrazolo[4,3-c]cinnolin-2-yl)-benzamide, of formula (B):

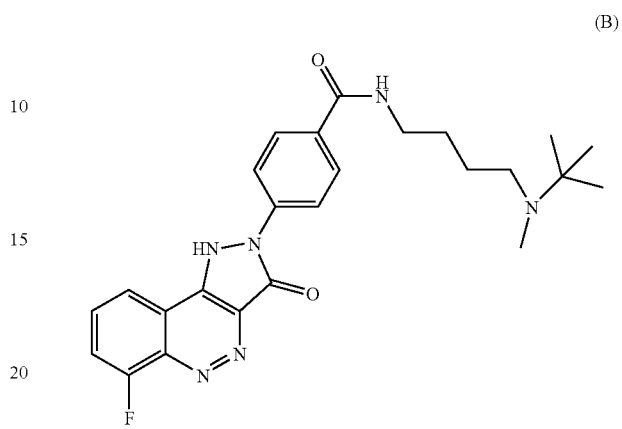

(B)

or a pharmaceutically or veterinarily acceptable salt or hydrate.

24. The orally administrable composition of claim 1 which is in unit dosage form.

25. The orally administrable composition of claim 1 which is in the form selected from the group consisting of a tablet, a capsule, a powder, a granule, a lozenge, a liquid, and a gel.

26. The orally administrable composition of claim 1 which is a liquid.

27. The orally administrable composition of claim 1 which is in the form of an aqueous suspension, an oily suspension, a solution, an emulsion, a syrup, or an elixir.

28. The orally administrable composition of claim 1 further comprising a binding agent.

29. The orally administrable composition of claim 28 wherein the binding agent is selected from the group consisting of syrup, acacia, gelatin, sorbitol, tragacanth, and polyvinyl-pyrrolidone.

30. The orally administrable composition of claim 1 further comprising a filler.

31. The orally administrable composition of claim 30 wherein the filler is selected from the group consisting of lactose, sugar, maize-starch, calcium phosphate, sorbitol and glycine.

32. The orally administrable composition of claim 1 which is a tablet.

33. The orally administrable composition of claim 32 further comprising a tableting lubricant.

34. The orally administrable composition of claim 33 wherein the tableting lubricant is selected from the group consisting of magnesium stearate, talc, polyethylene glycol, and silica.

35. The orally administrable composition of claim 32 wherein the tablet is coated.

36. The orally administrable composition of claim 1 further comprising a disintegrant.

37. The orally administrable composition of claim 36 wherein the disintegrant is potato starch.

38. The orally administrable composition of claim 1 further comprising a wetting agent.

39. The orally administrable composition of claim 38 wherein the wetting agent is sodium lauryl sulphate.

40. The orally administrable composition of claim 1 further comprising one or more additives selected from the group consisting of a suspending agent, an emulsifying agent, a non-aqueous vehicle, a preservative, a flavouring, and a colouring.

41. The orally administrable composition of claim 40 which comprises the suspending agent, wherein the suspending agent is selected from the group consisting of sorbitol, syrup, methyl cellulose, glucose syrup, and gelatin hydrogenated edible fats.

42. The orally administrable composition of claim 40 which comprises the emulsifying agent, wherein the emulsifying agent is selected from the group consisting of lecithin, sorbitan monooleate, and acacia.

43. The orally administrable composition of claim 40 which comprises the non-aqueous vehicle, wherein the non-aqueous vehicle is an edible oil.

44. The orally administrable composition of claim 43 wherein the edible oil is selected from the group consisting of almond oil and fractionated coconut oil.

45. The orally administrable composition of claim 43 wherein the non-aqueous vehicle is an oily ester.

46. The orally administrable composition of claim 45 wherein the oily ester is glycerine or propylene glycol.

47. The orally administrable composition of claim 40 which comprises the preservative, wherein the preservative is methyl or propyl p-hydroxybenzoate or sorbic acid.

48. The orally administrable composition of claim 22 which is a tablet.

* * * * *